United States Patent [19]

McCormick et al.

[11] Patent Number: 6,043,036

[45] Date of Patent: *Mar. 28, 2000

[54] METHOD OF SEQUENCING NUCLEIC ACIDS BY SHIFT REGISTERING

[75] Inventors: Randy M. McCormick, Santa Clara; Jonathan Briggs, Los Altos Hills, both of Calif.

[73] Assignee: Aclara Biosciences, Mountain View, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/977,931

[22] Filed: Nov. 24, 1997

Related U.S. Application Data

[63] Continuation of application No. 08/636,414, Apr. 23, 1996, abandoned.

[51] Int. Cl.$^7$ ............................. C12Q 1/68; C12P 19/34
[52] U.S. Cl. ................................. 435/6; 435/91.1
[58] Field of Search ........................ 435/6, 91.1

[56] References Cited

U.S. PATENT DOCUMENTS

| | | | |
|---|---|---|---|
| 4,811,218 | 3/1989 | Hunkapillar et al. | 364/413.01 |
| 4,865,968 | 9/1989 | Orgel et al. | 435/6 |
| 5,124,247 | 6/1992 | Ansorge | 435/6 |
| 5,273,638 | 12/1993 | Konrad et al. | 204/299 R |
| 5,409,811 | 4/1995 | Tabor et al. | 435/6 |
| 5,582,705 | 12/1996 | Yeung et al. | 204/603 |

*Primary Examiner*—Kenneth R. Horlick
*Attorney, Agent, or Firm*—McDonnell Boehnen Hulbert & Berghoff

[57] ABSTRACT

The present invention describes a method of sequencing nucleic acids in which mixtures of oligonucleotide fragments are derived from sequencing reactions using combinations of the 2',3'-dideoxynucleoside 5'-triphosphate or 3' deoxynucleoside 5'-triphosphate terminators and appropriate concentrations of four dNTPs (2'-deoxynucleoside 5' triphosphates, e.g., dATP, dCTP, dGTP, dTTP, dITP, 7-deaza-GTP). These fragments are generated by enzymatic extension of a primer hybridized to the single-stranded template DNA to be sequenced. In contrast to common slab gel sequencing methods, the method of the instant invention does not require precise alignment of the four separation sets of the terminated fragments to permit deduction of the DNA sequence. In addition, the method possesses inherent redundancy in the separations, which facilitates sequence assignment by resolving sequence uncertainties or anomalies.

28 Claims, 14 Drawing Sheets

METHOD OF SEQUENCING NUCLEIC ACIDS BY SHIFT REGISTERING

This application is a continuation, of application Ser. No. 08/636,414, filed Apr. 23, 1996, now abandoned.

BACKGROUND OF THE INVENTION

1. Field of the Invention

This invention relates to the field of sequencing nucleic acids.

2. Description of the Prior Art

One of the classic methods of sequencing DNA with a radioisotope label and slab gels was first described by Sanger et al. (F. Sanger, S. Niklen, and A. R. Coulson, *Proc. Nat. Acad. Sci.* 1977 74: 5643). Four individual sets of sequencing fragments, each terminating in one of the four 2',3'-dideoxynucleoside 5'-triphosphate, ddNTPs (2',3'-dideoxyguanosine 5-triphosphate, ddATP, 2',3'-dideoxycytidine 5'-triphosphate, ddCTP, 2',3'-dideoxyguanosine 5'-triphosphate, ddGTp, and 2',3'-dideoxythyrnidine 5'-triphosphate, ddTTP) are produced via enzymatic extension of a primer hybridized to the template DNA by sequential addition of template complementary 2'-deoxynucleoside 5'-triphosphates, dNTPs (dA, dC, dG and dT). A radioisotope label ($^{32}$P) is incorporated into each fragment via a labeled primer, dNTP, or ddNTP, such that when the four sets of fragments are separated in four adjacent lanes of an electrophoretic slab gel, the fragments can be visualized on photographic film. The resulting pattern that the fragments display must be properly aligned since sequence information is read from the relative position of the bands in the four gel lanes. Migration anomalies arising from bubbles in the gel matrix or "smiles" arising from temperature inhomogeneity within the gel during the separation make sequence reading an art. Highly accurate sequence determinations derived from these gels requires a high level of skill.

More recently, methods employing four different fluorescent labels have been described by Smith et al. (U.S. Pat. No. 5,171,534; *Nature* 1986 321(12): 674–679) and Prober et al. (U.S. Pat. No. 5,332,666; U.S. Pat. No. 5,306,618; U.S. Pat. No. 5,242,796; *Science* 1987 238: 336–341). These methods utilize four spectrally distinguishable fluorescent tags, each tag associated with one of the four nucleotide terminators. These tags are used to distinctly label each of the four sets of fragments, which can then be separated in a single electrophoretic run. These methods circumvent the lane alignment problems associated with the original Sanger dideoxy-mediated sequencing protocol, since all four sets of fragments are separated in a single lane of the electrophoretic gel. However, these methods require significantly more complex instrumentation than the original Sanger method since the partially overlapping sets of fragments must be photometrically monitored and the four emission wavelengths, "colors", associated with the four fluorophore labels must be distinguished to allow proper assignment of base identity (adenine (A), cytosine (C), guanine (G), or thymine (T)) and base position within the template DNA. In addition, four chemically-similar but spectrally-distinguishable fluorophore labels must be developed. The four labels must be chemically-similar, otherwise the four labels would impart different mobility shifts to the four sets of fragments resulting in migration order errors. Specific sets of fluorophore dyes useful for labeling the sequencing fragments in these methods are described by Fung et al. (U.S. Pat. No. 4,855,255), Hobbs et al. (U.S. Pat. No. 5,047,519), Menchen et al. (U.S. Pat. No. 5,188,934), Prober et al. (U.S. Pat. No. 5,242,796), and Bergot et al. (U.S. Pat. No. 5,366,860).

The previously described sequencing methods are based on simultaneous separation of a mixture of the four types of terminated sequence fragments and discrimination among the bases by the color of the sequencing fragment band. Numerous other sequencing methods based on separation of various combinations of the four types of terminated sequencing fragments have been developed. Orgel and Patrick (U.S. Pat. No. 4,865,968) demonstrated a sequencing method based on patterns obtained from three distinct sequencing mixtures derived from a template DNA. The first mixture contains oligonucleotide fragments derived from termination by all four 2',3'-dideoxynucteoside 5'-triphosphate terminators. The second mixture contains only those fragments derived from use of a first and a second 2',3'-dideoxynucleoside 5'-triphosphate terminator and the third set contains only those fragments derived from use of a first and a third 2',3'-dideoxynucleoside 5'-triphosphate terminator. These three mixtures are run in adjacent lanes of an electrophoretic slab gel and the DNA sequence of the template DNA is read from the relative migration order of the fragments in the three adjacent separations. These three separations must be properly aligned to obtain accurate sequence information. All fragments in the three mixtures contain a single label type.

Tabor and Richardson (U.S. Pat. No. 4,962,020) described a method of DNA sequencing in which the relative ratios of the 2',3'-dideoxynucleoside 5'-triphosphate terminators are varied in conjunction with the use of a modified T7 DNA polymerase. A manganese ion cofactor enables the maintainence of relatively constant label signal intensity (as measured in peak height) for the various series of oligonucleotide fragments in the mixture. In this way, a single sequencing reaction with different concentrations of ddA, ddC, ddG, and ddT terminators can be used to derive the sequence of a template DNA. A single label (fluorophore) is used in all reaction mixtures.

Ansorge (U.S. Pat. No. 5,124,247) developed a method of nucleic acid sequencing in which a single label is employed to monitor and distinguish individual bands in separations of mixtures of nucleic acids. Two mixtures, one containing ddA and ddG terminated fragments (A+G) and another containing ddC and ddT terminated fragments (C+T), are produced via enzymatic extension of a primer hybridized to the template DNA using a DNA polymerase. A single fluorophore label is attached to the primer or to one of the deoxynucleotides in the reaction mixture. Binary coding of the two sets of fragments in each mix is accomplished by employing different concentrations of the 2',3'-dideoxynucleoside 5'-triphosphate terminators in the two reactions. For example, in the A+G reaction, the ddA terminator is present in five-fold greater concentration than the ddG terminator. This results in ddA-terminated fragment signals that are fivefold greater than the signal generated by the ddG-terminated fragments. Thus, the ddA fragments can be distinguished from the ddG fragments in the same separation because the ddA fragments give signals, represented as peaks, that are five times the height (or five times the area) of the ddG terminated fragments. By running two sequencing reactions and two parallel separations of the fragments from these two reactions, the sequence information can be deduced from the peak order and the relative peak magnitudes. Proper alignment of the separations in two adjacent lanes of the electrophoretic gel is required to obtain accurate sequencing information.

Konrad and Pentoney (U.S. Pat. No. 5,273,638) described a similar approach in which two sets of sequencing reactions are prepared for each template DNA to be sequenced. Each reaction mixture contains three of the four possible 2',3'-dideoxynucleoside 5'-triphosphate terminator fragments, though the identity of the three terminators in the first reaction mixture (e.g., ddA, ddC, ddG) is different from the identity of the three terminators in the second reaction mixture (e.g. ddC, ddG, ddT). In addition, the relative concentrations of the three terminators in each mix are different (e.g. 4:1.7:0.7) such that the relative heights or areas of the resulting peaks in the separations of the mixtures are height- or area-coded. Thus, by comparing the relative magnitude of the heights (or areas) of the peaks in one of the separations, one can assign a nucleotide sequence to the pattern of peaks. Since peaks for one of the nucleotides will not be present in the separation, a second parallel separation of the second set of fragments is used to identify the relative positions of the omitted nucleotide of the first reaction and to resolve conflicts/anomalies arising from the peak height-encoding strategy.

Tabor and Richardson (U.S. Pat. No. 5,409,811) detailed a sequencing method utilizing a single mixture of three 2',3'-dideoxynucleoside 5'-triphosphate terminators, which differ in relative concentration in the sequencing mixture. The resulting 2',3'-dideoxynucleoside 5'-triphosphate-terminated fragments can be differentiated by the relative intensities of the bands in the separation.

Mathies et al. (U.S. Pat. No. 5,436,130) described a sequencing method using a binary coding scheme in conjunction with two fluorophore labels. The mixture of four 2',3'-dideoxynucleoside 5'-triphosphate terminated fragments is separated in a single lane or channel of electrophoresis. The individual nucleotides of the DNA are distinguished by a combination of the intensity and the spectral characteristics (ratio of color at two wavelengths due to the presence of the two fluorophores in differing ratios) of the peaks.

To obtain useful sequence data, many of the above sequencing methods require proper alignment of the separation patterns derived from the various mixtures of terminated sequencing fragments run in adjacent lanes of an electrophoretic gel. Problems with misalignment between lanes in electrophoretic separations of nucleic acid sequencing fragments can be caused by inclusion of a gas bubble in an electrophoretic gel lane, lane-to-lane variation of the temperature of the gel during separation, variation in the extent of polymerization of the gel from lane to lane, variation in the ionic composition of the samples loaded into different lanes, and variation in the depths of the wells into which the samples are loaded. Hara (U.S. Pat. No. 4,720,786) described a method of correcting for these offset distortions between adjacent lanes in an electrophoretic gel based on the resolution of bands corresponding to the smaller oligonucleotide fragments in the lower portion of the electrophoretic separations. The method relies on the assumption that because the band spacing is greater in the lower portion of the separation, the proper band migration pattern can be determined even in the presence of offset distortions in one or more of the electrophoretic lanes. Once the degree of offset distortion has been established in this portion of the gel, a correction factor can be derived and applied to other gel lanes resulting in properly ordered band patterns. Because the offset distortion is determined for bands in the lower part of the gel, and because the degree of distortion varies from the bottom to the top of the gel, the correction factor for bands in the middle and at the top of the gel must be extrapolated from data derived from bands at the bottom of the gel. The extent of offset distortion must vary in a predictable and consistent manner for this alignment protocol to be effective.

Fujii (U.S. Pat. No. 5,419,825) described an apparatus and method for sequencing which relies on calibration coefficients for time bases of respective electrophoresis lanes which are evaluated from differences between positions of signals in a range known to cause no sequence inversion. In essence, Fujii determines "correction factors" for the various electrophoretic lanes based on the migration patterns for the highest mobility (smallest) fragments in each lane, and on the assumption that no band migration order inversion has occurred for these smallest fragments. Once these correction factors have been determined, they are applied to the next group of electrophoretic bands reaching the detector to correct for any mobility differences between lanes for this next group of bands. Once corrected, these bands are used to derive new correction factors which can be applied to the next group of peaks reaching the detector.

Both correction methods rely on the assumption that the relative migration order of the highest mobility bands (smallest fragments) in each of the four electrophoretic separations that are to be aligned is correct. Both methods also rely on the assumption that changes in electrophoretic conditions during the course of the separation (e.g. temperature fluctuations) affect all four electrophoretic separations equally and thus can be compensated by calculated correction factors. Neither method could be used to align electrophoretic bands obtained in four sequential separations in which the fragments were separated on the same electrophoretic media (e.g. separated by capillary electrophoresis in a single capillary), since temporal variations in separation conditions are not likely to be reproducible in sequential separations.

In contrast, the method of the present invention makes no assumptions about the temporal migration order in any region of the four separations. The method of the instant invention makes no assumptions about the effect of fluctuations in separation conditions over the course the separation. Temporal changes in separation conditions during the electrophoresis run will be reflected in minute changes in the band spacing pattern in a given separation which may result in a local expansion or contraction of the peak spacing. This will be corrected internally in that separation but will have no impact on separation patterns for the other three bases. Thus, the invention method can be applied not only to separations run simultaneously in adjacent lanes of an electrophoretic slab gel, but can also be utilized to align separations run sequentially in the same electrophoretic capillary or run in serial or parallel fashion on two, three, or four different capillaries or slab gels.

SUMMARY OF THE INVENTION

The invention demonstrates a method of sequencing nucleic acids which employs mixtures of labeled oligonucleotide fragments derived from sequencing reactions terminating in combinations of nucleotide terminators, such as 2',3'-dideoxynucleoside 5'-triphosphates (ddNTPs) or 3'-deoxynucleoside 5'-triphosphates (3'-dNTPs). Nucleotide terminators prevent further enzymatic extension of a growing nucleotide chain. Fragments are generated by enzymatic extension of a primer hybridized to the template DNA to be sequenced utilizing appropriate concentrations of four 2'-dNTPs (2'-deoxynucleoside 5'-triphosphates; for example dATP, dCTP, dGTP, dTTP, dITP, 7-deaza-dGTP). The preferred method of the invention uses the four possible combinations of three 2',3'-dideoxynucleoside 5'-triphosphate (ddNTPs or ddN) terminators to generate the oligonucleotide fragments. In this preferred method, four unique mixtures of sequencing fragments containing dd/AddC/ddG, ddA/ddC/ddT, ddA/ddG/ddT, and ddC/ddG/ddT terminated fragments are produced and these mixtures are individually separated electrophoretically in parallel or sequential runs. Each of the mixtures yields a unique pattern of labeled oligonucleotide fragments, sequence string, which can be used to establish a relative spacing of fragments in each separation. The identity and location of one type of nucleotide base in the sequence can be deduced in each sequence string by the absence of a known set of fragments in each separation. The sequence of the template nucleic acid can then be deduced from the unique alignment of the individual sequence strings obtained from the four fragment separation patterns.

The method of the present invention is useful for deducing nucleic acid sequence data from separation methods that utilize only one type of detection label or tag moiety (e.g. a single fluorophore, chromophore or radioisotope) on the nucleic acid fragments. This method may also be utilized in methodologies based on multiple types of labels or tags. In contrast to common slab get sequencing methods based on the Sanger sequencing protocol, the method of the instant invention is unique in that it does not require that the separations derived from the four sets of fragments be run in precise alignment to permit determination of the template DNA sequence. In addition, the method of this invention possesses inherent redundancy in the separations which facilitates resolution of sequence uncertainties or anomalies.

The foregoing merely summarizes certain aspects of the invention and is not intended, nor should it be construed, as limiting the invention in any manner. All patents and publications recited in the specification are hereby incorporated by reference in their entirety.

BRIEF DESCRIPTION OF THE DRAWINGS

FIGS. 1A–1B shows the separation of the 3-component 2',3'-dideoxynucleoside 5'-triphosphate-terminated sequencing fragments derived from the mixture containing ddC, ddG, and ddT terminators and thus encodes the sequence pattern for the dA nucleotides in the template DNA.

FIGS. 1C–1D shows the separation of the 3-component 2',3'-dideoxynucleoside 5'-triphosphate-terminated sequencing fragments derived from the mixture containing ddA, ddG, and ddT terminators and thus encodes the sequence pattern for the dC nucleotides in the template DNA.

FIG. 2A illustrates the nonaligned sequence strings derived from each of the four separations shown in FIG. 1.

FIGS. 2B–2C shows the aligned sequence strings as well as the DNA sequence derived from combination of the properly aligned strings.

DETAILED DESCRIPTION OF THE INVENTION

Figure 1A:
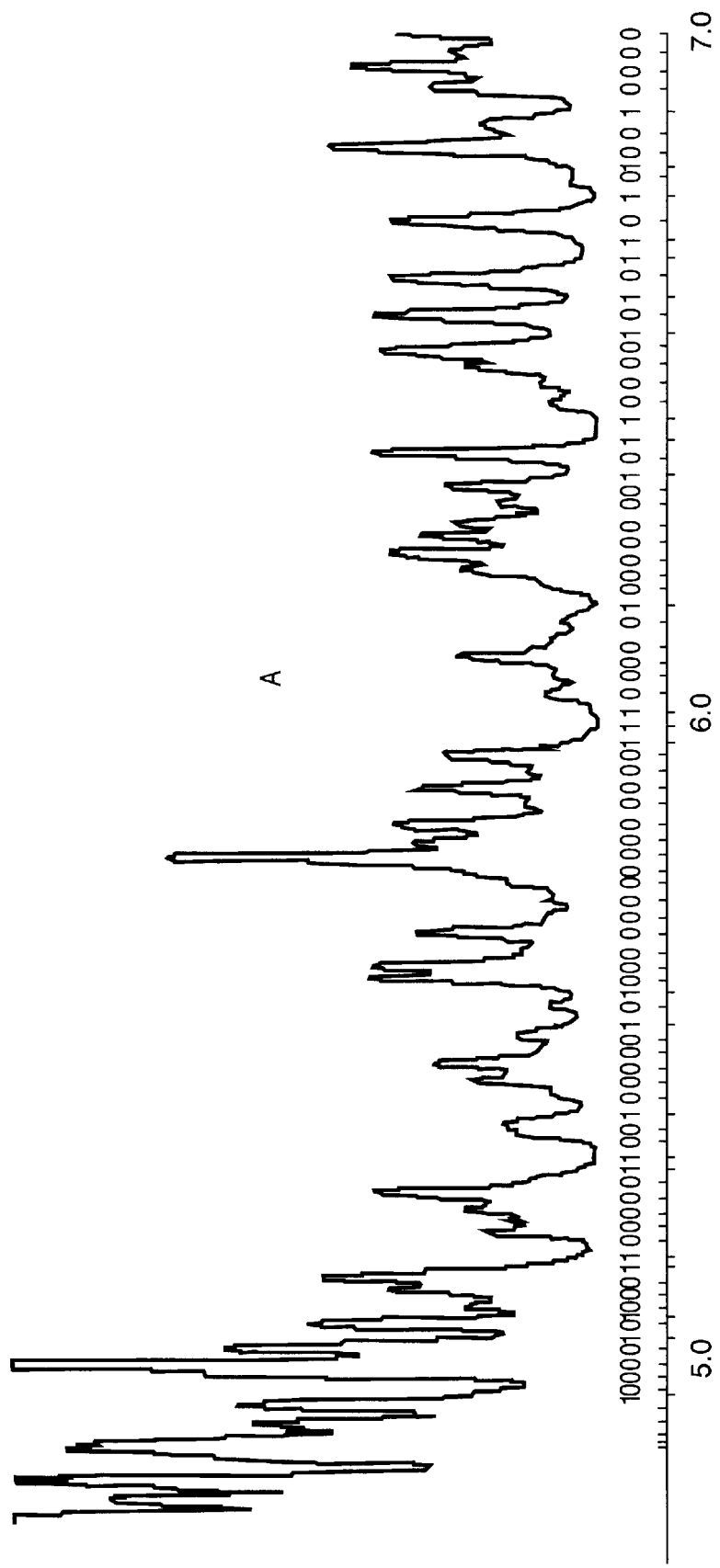
FIGS. 1A–1D illustrate the separation achieved on the four sets of 3-component 2',3'-dideoxynucleoside 5'-triphosphate terminated sequencing fragments derived from the preferred embodiment of the instant invention.
Figure 1B:
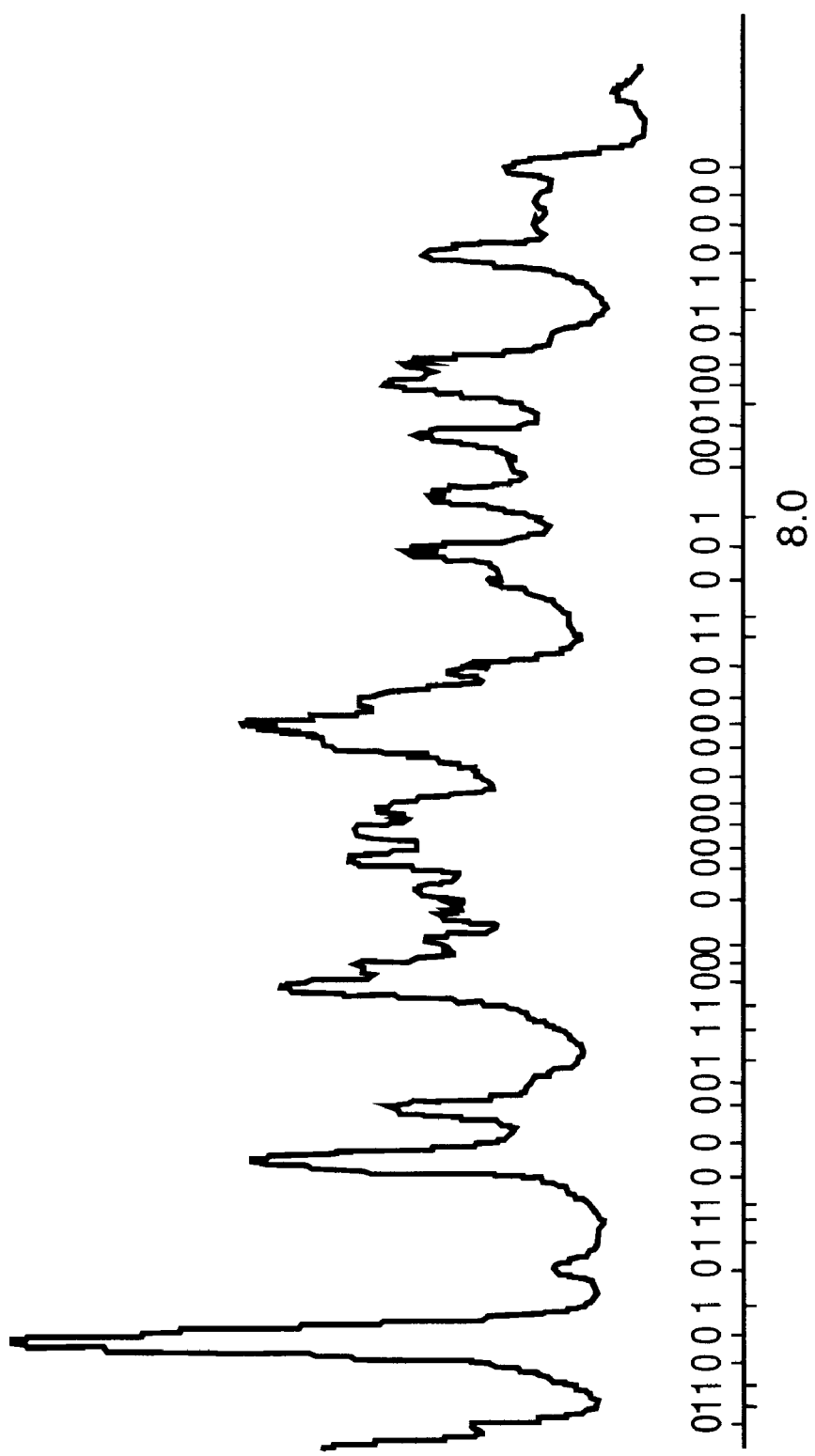
Figure 1C:
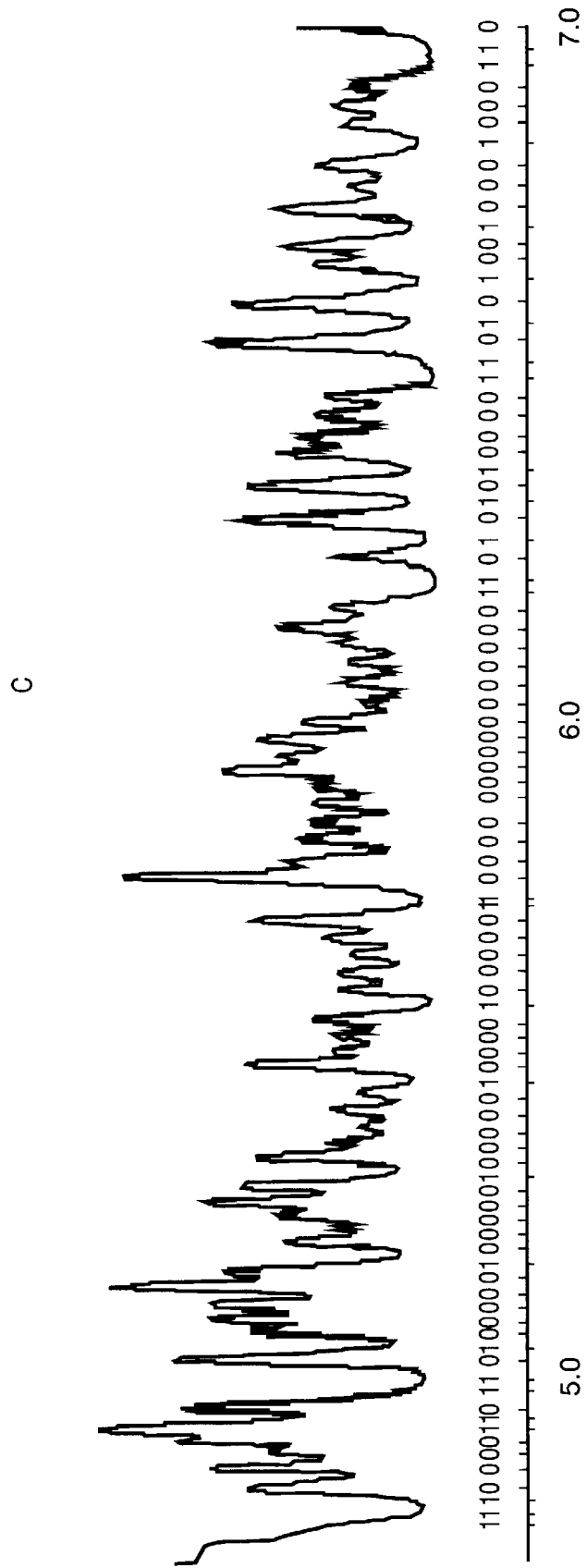
Figure 1D:
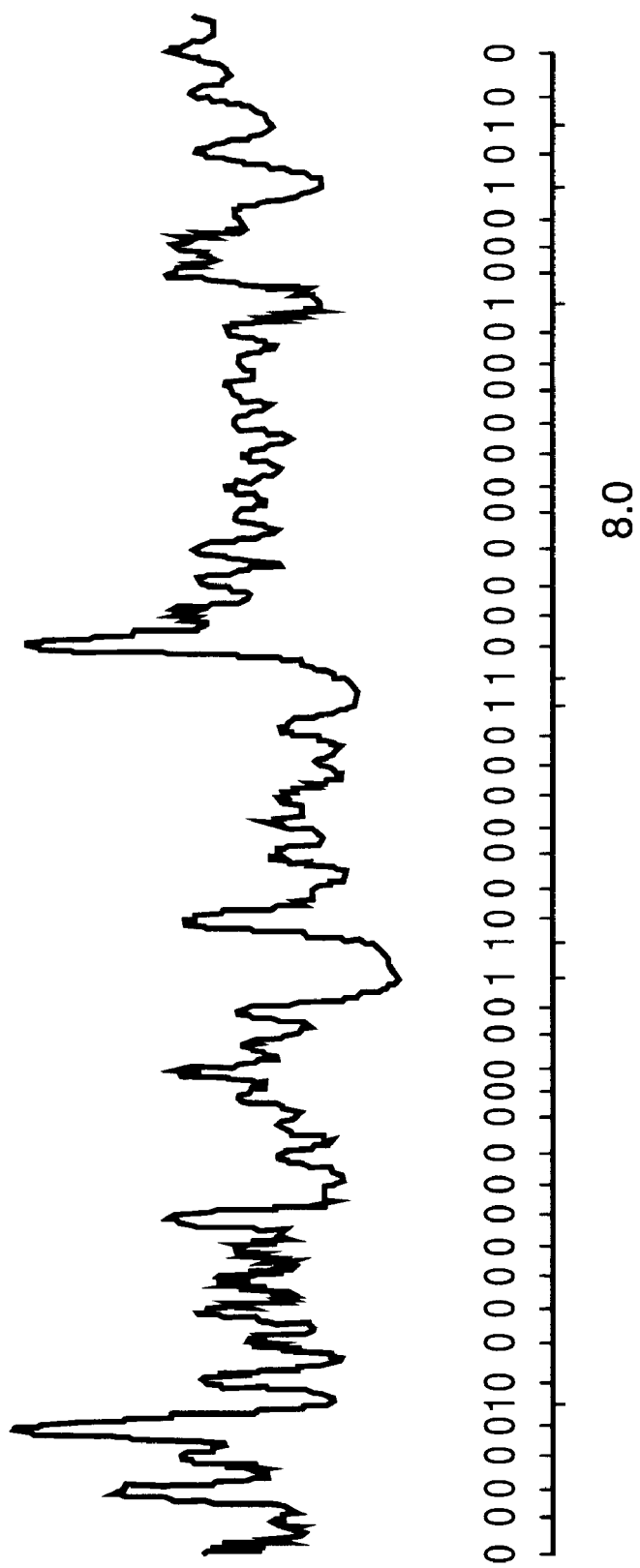
Figure 1E:
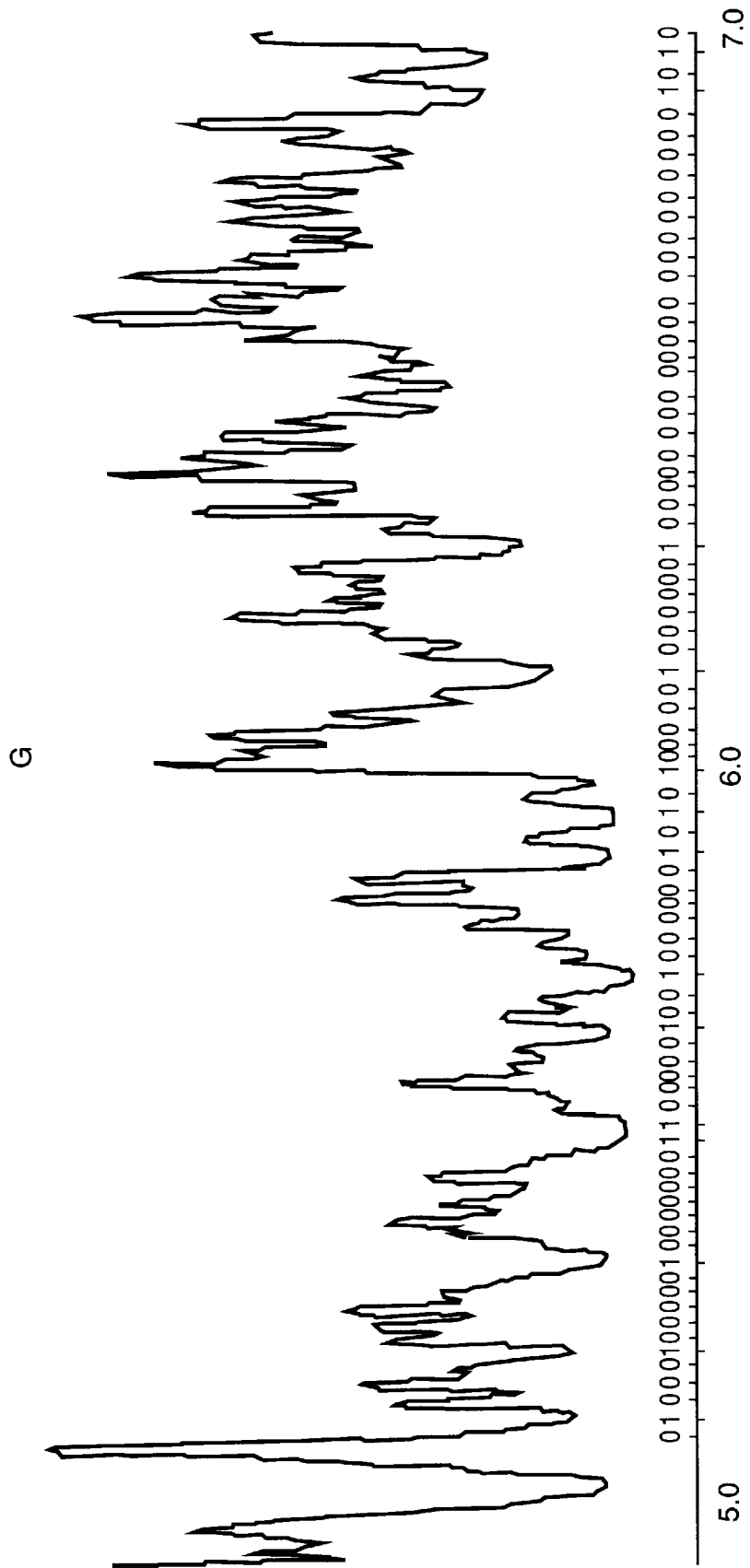
FIGS. 1E–1F shows the separation of the 3-component 2',3'-dideoxynucleoside 5'-triphosphate-terminated sequencing fragments derived from the mixture containing ddA, ddC, and ddT terminators and thus encodes the sequence pattern for the dG nucleotides in the template DNA.
Figure 1F:
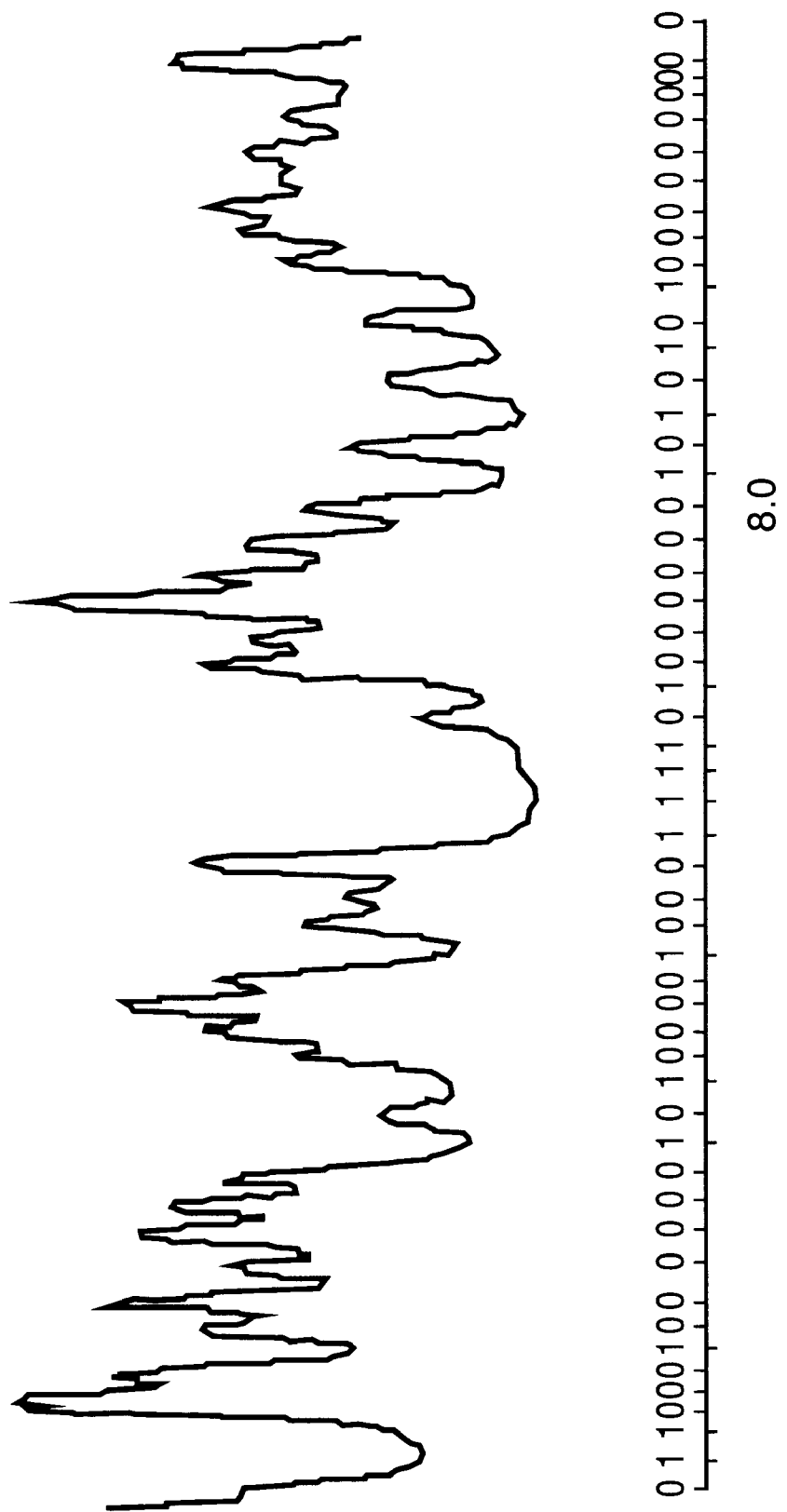
Figure 1G:
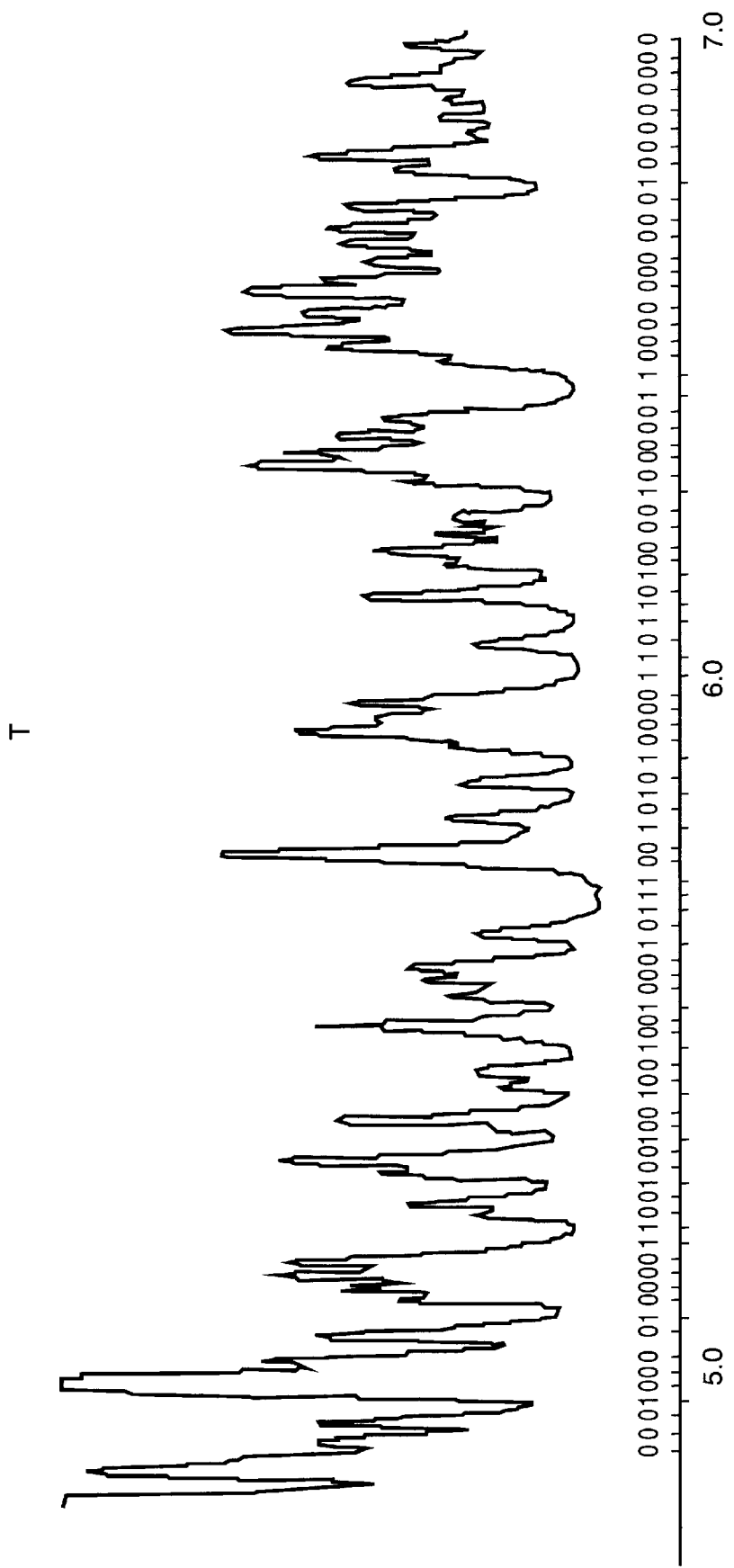
FIGS. 1G–1H shows the separation of the 3-component 2',3'-dideoxynucleoside 5'-triphosphate-terminated sequencing fragments derived from the mixture containing ddA, ddC, and ddG terminators and thus encodes the sequence pattern for the dT nucleotides in the template DNA. The separation patterns are used to produce sequence strings for each base, and these are shown along the abscissa of each separation.
Figure 1H:
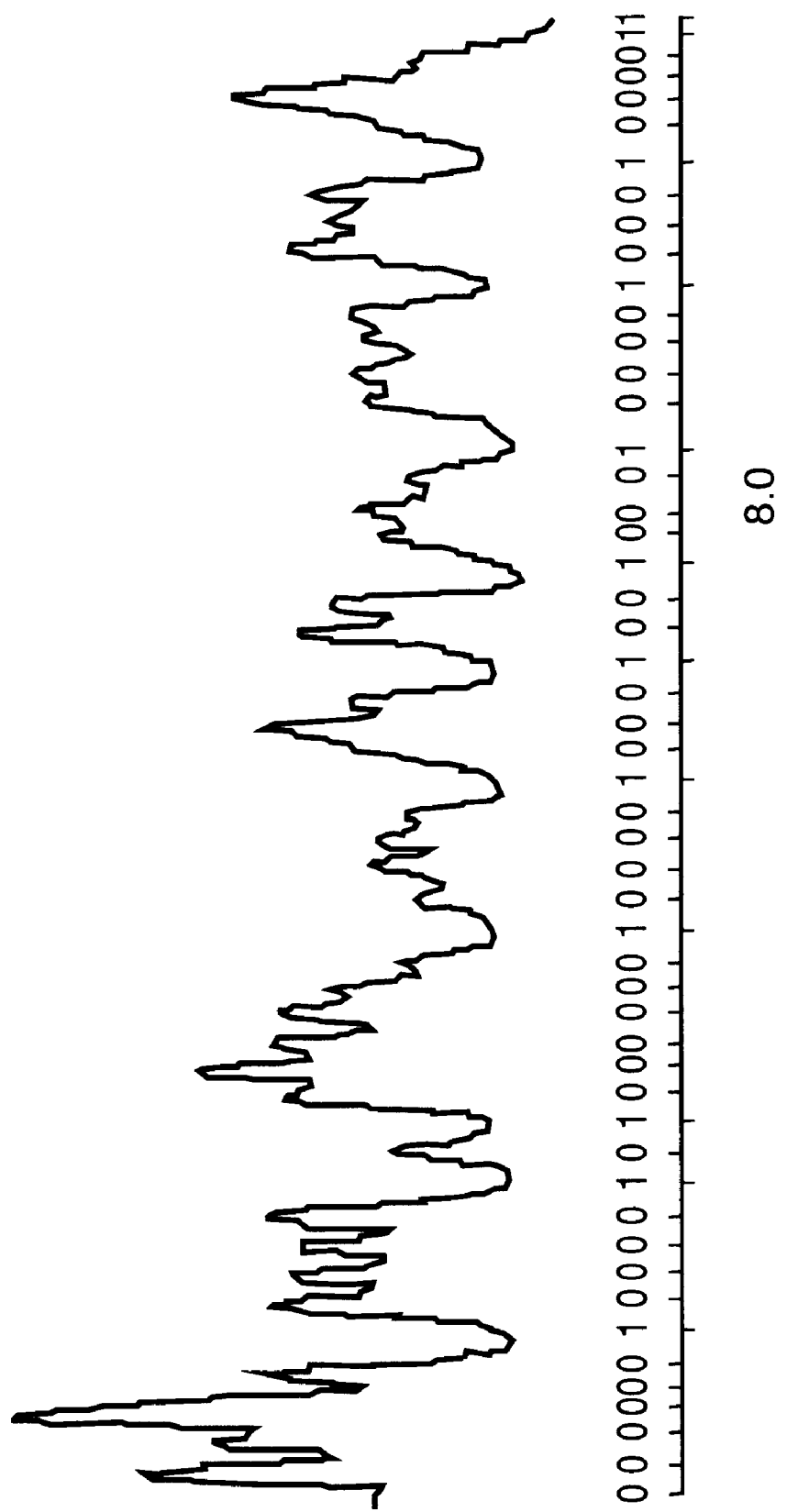

Generally, the preferred method of the instant invention is based on a modified Sanger 2',3'-dideoxynucleoside 5'-triphosphate mediated sequencing protocol using enzymatic extension of a primer hybridized to the template DNA to be sequenced. This method utilizes a DNA polymerase to synthesize a complementary copy of a portion of the DNA template. DNA polymerases cannot initiate polymerization of complementary oligonucleotide fragments without the presence of a primer sequence. Primers are oligonucleotides complementary to a portion of the nucleic acid template and provide a 3' terminus for addition of 2'-deoxynucleoside 5'-triphosphates by the DNA polymerase. These 2'-deoxynucleoside 5'-triphosphates are substrates for the polymerization reaction and are added to the growing chain by their ability to base-pair with the nucleic acid template. Chain growth involves the formation of a phosphodiester bridge between the 3'-hydroxyl group at the growing end of the primer and the 5'-phosphate group of the incoming dNTP. Thus, complementary primers provide the start site for initiation of polymerization and dNTPs are incorporated into a growing chain based on their ability to base-pair with the nucleic acid template. Polymerization will continue unabated unless a nucleotide terminator is present to terminate the polymerization reaction.

The dideoxy sequencing method capitalizes on the ability of the polymerase to use 2',3'-dideoxynucleoside 5-triphosphates (ddNTPs) as substrates. Incorporation of a ddNTP into a growing chain prevents further extension of the chain, because the 3'-hydroxyl group required for the formation of the phosphodiester bond has been replaced with a hydrogen atom. Using the appropriate ratio of dNTPs and ddNTPs in the reaction mixture permits the termination of the elongating primer at each occurance of the base in the template DNA corresponding to the included complementary ddNTP. Standard dideoxy sequencing requires four reaction mixes, each containing primer, dNTPs (dATP, dCTP, dGTP and dTTP), template, polymerase, buffer and one of the four ddNTPs (ddATP, ddCTP, ddGTP and ddTTP). The method requires that primer, dNTP, or ddNTP contain a colorimetric, fluorometric or radiometric label, which can be detected. Thus, after the reaction, each of the four mixes contains a population of labeled extended primer chains, all of which have a fixed 5' end determined by the annealed primer and a variable 3' end terminating at a specific ddNTP. Each of the four mixtures of oligonucleotide fragments can then be separated according to their length, usually by electrophoretic means. In the standard technique the four mixtures are electrophoresed in separate lanes on a gel and then detected in some fashion according to how the fragments have been labeled. The linear order of the nucleotides in the template DNA can be deduced by the relative positions of the detected labeled oligonucleotide fragments. The preferred method of the present invention utilizes four unique sets of labeled sequencing fragments, each containing three of the four 2',3'-dideoxynucleoside 5'-triphosphate terminated fragments in approximately equal concentrations (unlike the standard method which utilizes four reaction mixtures, each with a single ddNTP type). Thus, four different sets of sequencing fragments (set A=fragments terminated by the ddC, ddG, ddT mix; set C=fragments terminated by the ddA, ddG, ddT mix; set G=fragments terminated by the ddA, ddC, ddT mix; set T=fragments terminated by the ddA, ddC, ddG mix) are produced in the sequencing reactions. These labeled fragments are separated according to size, each set determined independently by performing the separations in a temporally or spatially distinct manner. Detection of the distinct pattern derived from each set of separations produces a pattern of the linear order of one of the nucleotides in the template DNA. These patterns can be compared and combined with each other to deduce the template sequence. There is a threefold redundancy in sequence information since each set of dideox-terminated fragments is present in three of the four sequencing mixtures.

Another useful implementation of the instant invention is based on six sets of labeled oligonucleotide fragments produced from the template DNA in a set of six reaction mixtures. Set one is comprised of labeled oligonucleotide fragments produced with ddA and ddC terminators, set two is comprised of labeled oligonucleotide fragments produced with ddA and ddG terminators, set three is comprised of labeled oligonucleotide fragments produced from ddA and ddT terminators, set four is comprised of labeled oligonucleotide fragments produced from ddC and ddG terminators, set five is comprised of labeled oligonucleotide fragments produced from ddC and ddT terminators, and set six is comprised of labeled oligonucleotide fragments produced from ddG and ddT terminators. These labeled fragments are separated according to size, each set determined independently by performing the separations in a temporally or spatially distinct manner. Detection of the distinct pattern derived from each set of separations produces a pattern of the linear order of one of the nucleotides from the template DNA, and these patterns can be compared and combined with each other to deduce the template sequence. Yet another useful implementation is based on a set of four reaction mixtures selected from the following six possible combinations: combination one being comprised of labeled oligonucleotide fragments produced with ddA and ddC terminators, combination two being comprised of labeled oligonucleotide fragments produced with ddA and ddG terminators, combination three being comprised of labeled oligonucleotide fragments produced from ddA and ddT terminators, combination four being comprised of labeled oligonucleotide fragments produced from ddC and ddG terminators, combination five being comprised of labeled oligonucleotide fragments produced from ddC and ddT terminators, and combination six being comprised of labeled oligonucleotide fragments produced from ddG and ddT terminators. Each of the terminators ddA, ddC, ddG, and ddT is represented in two of the four reaction mixtures. For example, one possible combination of four reaction mixtures would be ddA/ddC, ddC/ddG, ddG/ddT, and ddT/ddA. Yet another possible combination of four mixtures would be ddA/ddG, ddC/ddT, ddA/ddC, and ddG/ddT. There are at least four useful combinations using this strategy. In all cases recited above, alternative 2',3'-dideoxynucleoside 5'-triphosphate terminators, such as 2',3'-dideoxyinosine 5'-triphosphate (ddITP), modified analogs of 2',3'-dideoxynucleoside 5'-triphosphate terminators such as fluorophore-modified (DyeDeoxy™ Terminators, Perkin-Elmer/ABI) or biotin-modified (GATC, Konstanz, Germany) terminators or 3'-deoxynucleoside 5'-triphosphate terminators or analogs thereof, could also be utilized.

These sets of four or six sequencing reaction fragments are produced via enzymatic extension of an oligonucleotide primer hybridized to the template DNA, the sequence of which is to be determined. Also present in these reaction mixtures are 2'-deoxynucleoside 5'-triphosphates and 2',3'-dideoxynucleoside 5'-triphosphates or 3'-deoxynucleoside 5'-triphosphates at appropriate concentrations, as well as enzymes, cofactor, and buffer salts. The sets of four or six fragments may be prepared by four or six individual reactions, each reaction containing two or three nucleotide terminators. Alternatively, four sequencing reactions can be run, each containing only one nucleotide terminator and, at the conclusion of the reactions, the mixtures of the two or three terminated fragments prepared by blending aliquots of the appropriate individual reaction products to produce the two or three component mixtures.

The template DNA used in the present invention can be prepared by any number of well known methods (see, for example, Sambrook et al., *Molecular Cloning: A Laboratory Manual*, 2nd edition, 1989, Cold Spring Harbor Press, Cold Spring Harbor, N.Y., Chapter 13). Methods such as molecular cloning of the DNA in an appropriate vector or DNA amplification via Polymerase Chain Reaction (PCR™) are among the suitable methods. Single stranded templates can be generated either by using specialized vectors (M13 derivatives) or by denaturing double stranded templates with heat or alkali.

Primers suitable for use in the instant invention can be conventional oligonucleotide primers, radiolabeled primers, or biotin, chromophore- or fluorophore-labeled primers (available from any of a number of suppliers such as PE/ABI (Foster City, Calif.), Keystone Scientific (Menlo Park, Calif.), Bio-Synthesis (Lewisville, Tex.), Genemed (South San Francisco, Calif.). Primer length, dictated by the requirements for producing a stable and unique primer-template duplex, can vary between ~6 nucleotides to >30 nucleotides.

Chain-extension terminators suitable for use in the present invention include the 2',3'-dideoxynucleoside 5'-triphosphates, 3'-deoxynucleoside 5'-triphosphates (e.g., cordycepin), radiolabeled 2',3'-dideoxynucleoside 5'-triphosphates (supplied by New England Nuclear, Billerica, Mass. or Amersham Life Sciences, Arlington Heights, Ill.) or chromophore- or fluorophore-modified analogs of the 3'-deoxynucleoside 5'-triphosphates or the 2',3'-dideoxynucleoside 5'-triphosphate such as the DyeDeoxy™ terminators supplied by PE/Applied Biosystems Inc. (Foster City, Calif.). The preferred method would contain the ddTP terminators in approximately equal concentrations since this strategy would produce more uniform peak intensities throughout the separations, thereby facilitating identification of the locations or positions where peaks in each separation associated with the absent 2',3'-dideoxynucleoside 5'-triphosphate terminator are situated.

Labels suitable for incorporation into the sequencing fragments of the invention for detection purposes can include radioisotopes (e.g., $^{32}P$, $^{35}S$), which can be incorporated into the primer, into the terminator, or into one or more of the 2'-deoxynucleoside 5'-triphosphates as $\alpha$-$^{32}P$-dNTP or $\alpha$-$^{35}S$-dNTP. Suitable labels also include a chromophore or fluorophore incorporated on or near the 5' terminus of the primer or incorporated in the terminator or incorporated as a modified dNTP (e.g. Fluore-dATP or Cy5-dATP, available from Pharmacia, Piscataway, N.J.). Numerous fluorophore labels could be employed in the sequencing process to tag the sequencing fragments for detection purposes. For example, appropriate fluorophores include but are not limited to fluorescein, JOE™, FAM™, ROX™, Texas Red™, FITC, NBD, CY-5, or IR-440, available from Molecular Probes, Inc., Eugene, Oreg.; Li-Cor, Inc., Lincoln, Nebr.; Biological Detection Systems, Inc., Gaithersburg, Md.

Labeling methods suitable for the invention are based on a detectable label (fluorophore, chromophore, radioisotope) which can be chemically attached to the primer, to the terminators, or to one of the deoxynucleotides present in the sequencing reaction mixture. The preferred method of labeling would be to attach a fluorophore or isotope label to either the primer or the terminator (or both), since this strategy will produce more uniform peak intensities throughout the separations, thereby facilitating identification of the locations or positions where peaks in each separation associated with the absent terminator are situated.

Labeling of oligonucleotide chain extension fragments can employ a single label type or multiple label types depending on the detection system utilized. In the preferred embodiment, the fragments generated from the four sets of sequencing reactions (set A=fragments terminated by the ddC, ddG, ddT mix; set C=fragments terminated by the ddA, ddG, ddT mix; set G=fragments terminated by the ddA, ddC, ddT mix and set T=fragments terminated by the ddA, ddC, ddG mix) contain the same label. For example, labeled primers, labeled dNTPs or labeled ddNTPs containing a single type of label would be used in all sequencing reaction mixes. The fragments generated from the polymerization reactions would all contain the same label irrespective of which terminator was incorporated. In another embodiment, the four sets of sequencing reactions would generate oligonucleotide fragments that did not contain identical labels, but rather contained labels characteristic of a particular terminator. For example, the four sets of sequencing reactions would be run in which each ddNTP has a label different and distinguishable from the other ddNTPs in the reaction mix.

A variety of enzyme polymerases can be used in the present invention, including but not limited to the Klenow fragment of *E. coli* DNA Polymerase I, AMV (Avian Myeloblastosis Virus) Reverse Transcriptase, *Taq* (*Thermus aquaticus*) DNA Polymerase, *Bca* DNA Polymerase, *Tth* (*Thermus thernophilus*) DNA Polymerase, or modified analogs of T7 DNA Polymerase such as Sequenase™ Ver 1.0 or Ver 2.0. A preferred enzyme would be a genetically-modified T7 DNA Polymerase (Sequenase™ Ver. 2.0, United States Biochemical, Cleveland, Ohio) used in conjunction with manganese ion as cofactor (S. Tabor, C. C. Richardson, *Proc. Natl. Acad. Sci. USA*, 1989 86 4076–4080). This combination will produce more uniform peak intensities throughout the separations, thereby facilitating identification of the locations in the separations where peaks are absent. For fragments generated using a cycle sequencing protocol, the preferred enzyme is Thermo Sequenase™ which incorporates ddNTPs at rates that are independent of the neighboring sequence, resulting in uniform peak heights. Increase base calling accuracy is facilitated, thereby increasing read length.

Numerous protocols may be used to produce the sets of sequencing fragments. An example of a detailed procedure useful for this process can be found in the Sequenase™ Version 2.0 DNA Sequencing Kit Manual, "Step-By-Step Protocol For DNA Sequencing With Sequenase™ Version 2.0 T7 DNA Polymerase", 9th Ed., available from United States Biochemical, Cleveland, Ohio. Sets of sequencing fragments are produced by first annealing the primer to the single-stranded template DNA. The annealed DNA is then combined with the appropriate mixture of 2'-dNTPs, ddNTPs or 3'-dNTPs, enzyme(s), and buffers, and incubated at an appropriate temperature (e.g., 37° C.) for an appropriate duration of time (typically 5 minutes). The incubation process activates the polymerase to incorporate the dNTPs into the elongating complementary chain initiated by the primer. The ddNTPs are incorporated into a proportion of the elongating chains, thereby terminating the elongation of these chains and forming the sets of labeled oligonucleotide fragments. At the end of the incubation process, the extension reactions are halted by addition of formamide and EDTA, the latter component sequestering the $Mn^{2+}$ or $Mg^{2+}$ cofactor required for polymerase activity. These mixtures are then heated to denature the double-stranded DNA molecules in the sequencing mixtures and the denatured mixtures are then quick-chilled on ice to deter renaturation. The sequencing mixtures are then ready for the separation step.

Alternatively, labeled oligonucleotide fragments can be generated by the linear polymerase chain reaction utilizing thermostable DNA polymerase, appropriate buffer conditions and a single oligonucleotide primer (V. Murray, Nucleic Acids Res. 1989 17(21): 8889). This "cycle sequencing" method utilizes a template derived from amplification of a target sequence by the polymerase chain reaction (PCR™). The PCR™ template is added to a mixture of thermostable polymerase, reaction buffer and sequencing primer and distributed into termination mixtures containing dNTPs and the appropriate concentration and distribution of ddNTPs. These reactions are then subjected to approximately ten cycles of denaturation, annealing and polymerization (a typical cycling protocol is: 1 minute denaturation @ 94° C., 1 minute annealing @ 94° C. and 2 minutes polymerization @ 72° C.). Cycling increases the amount of sequencing products by effectively reusing the template DNA. After thermocycling, these reactions are halted with a formamide stop solution, denatured @ 94° C. for two minutes and then subjected to a separation procedure.

For the separation of the sets of sequencing fragments, the set of four or six sequencing mixtures could be run on four or six lanes of an electrophoretic slab gel or electrophoretic tube gels. Methods and techniques suitable for preparing polyacrylamide gels useful for electrophoretic separation of sequencing fragments are known in the art (see, for example, Sambrook et al., *Molecular Cloning: A Laboratory Manual*, 2nd edition, 1989, Cold Spring Harbor Press, Cold Spring Harbor, N.Y., Chapter 13.; R. W. Davis, "DNA Sequencing", in *Gel Electrophoresis of Nucleic Acids*, D. Rickwood and B. D. Hames, Ed., 1982, IRL Press, Washington, D.C., Chapter 4).

The set of sequencing reactions could be run in parallel on a set of essentially identical capillary columns used in capillary electrophoresis. Alternatively, the set of fragments could be run sequentially on a single capillary column used in capillary electrophoresis. The sequencing fragments can be separated on a gel-filled capillary, in which a polyacrylamide gel is formed by polymerization of acrylamide inside a small-bore capillary column. Alternatively, a polymer-based sieving buffer, which is prepared by dissolving an appropriate polymer (e.g., polyacrylamide, polyethylene oxide, etc.) in an appropriate background electrolyte buffer (e.g., 1X TBE) could be used as a separation medium. A preferred method of separation of the sets of sequencing fragments is by parallel separation on a set of four capillary electrophoresis columns using a sieving polymer solution. Methods and techniques suitable for preparing gel-filled capillaries, coated capillaries, and polymer-based sieving media are known in the art (see, for example, N. J. Dovichi, "Capillary Gel Electrophoresis for DNA Sequencing: Separation and Detection", in *Handbook of Capillary Electrophoresis*, J. P. Landers, Ed., 1994, CRC Press, Inc., Boca Raton, Fla., Chapter 14).

Injection of a portion of the sequencing sample into the capillary can be accomplished by several known methods. The preferred method of sample injection is to immerse the cathode end of the capillary into the sequencing reaction mixture and to apply a specified voltage for a timed duration. This method of injection, termed electrokinetic, electrormigration or electroinjection, is known in the art and is suitable for introducing samples into gel-filled capillaries or into capillaries filled with polymer-based sieving buffers. A second type of injection, hydrostatic or pressure injection, is effected by applying differential pressure across the capillary with the cathode end of the capillary immersed in the sample. The differential pressure may be accomplished by applying positive pressure to the injection end of the capillary or by applying vacuum (negative pressure) to the distal end of the capillary or by applying a combination of both pressure and vacuum to the appropriate ends of the capillary. Sample introduction in slab gel electrophoresis or tube gel electrophoresis is usually accomplished by pipetting an aliquot of the sample into a "well" formed in the gel matrix during the polymerization process. Typically, sample volumes in the microliter range ($\mu$L) are loaded onto the slab gels whereas samples of nanoliter (nL) volume are loaded into capillary electrophoresis columns.

Separations are achieved by applying an electric field across the electrophoretic separation medium for an appropriate duration of time. The magnitude of the electric field varies, depending upon the type of separation matrix chosen. For example, an appropriate electric field for a polyacrylamide slab gel might be 10 V/cm, whereas an appropriate electric field for a capillary/sieving buffer might be 300 V/cm. The duration of the application of the electric field will vary, ranging from 6–16 hours for a polyacrylamide slab gel to 5–10 minutes for a capillary-based separation.

Detection of the various fragments in the separations also varies with the separation method and the type of label used. For polyacrylamnide slab gels, autoradiographic detection of the radiolabeled fragments of the sequencing mixtures is possible. This involves exposure of the polyacrylamide slab gel to a sheet of photographic film for a defined duration of time, such that nuclear particles derived from radioactive decay of the radioisotope label in the labeled oligonucleotide fragment can darken the photographic film to produce a replica of the fragment separation on the film substrate. The separated fragments appear as discrete bands on the film surface. Fluorophore-labeled sequencing fragments can be detected in polyacrylamide slab gels by either lamp- or laser-based excitation of the sequencing fragments as they traverse the slab gel and migrate past a fixed detection point. Commercial instruments for detection of fluorophore-labeled fragments are available from a number of instrument suppliers (e.g., Li-Cor, Inc., Lincoln, Nebr.; Pharmacia Biotech, Piscataway, N.J.; Perkin-Elmer/Applied Biosystems Inc., Foster City, Calif.; Molecular Dynamics, Inc., Sunnyvale, Calif.). Finally, for capillary-based separations, detection can be accomplished via laser-induced fluorescence. A commercially available instrument suitable for this purpose is available from Beckman Instruments, Fullerton, Calif.

In fluorometric and calorimetric detection systems, signals generated by labeled sequencing fragments are often detected and recorded as peaks, for which height or area corresponds to the signal intensity. Thus, following separation of the sets of sequencing fragments, the data is analyzed to determine the relative peak spacing throughout the separation. This can be accomplished by placing a tick mark at a position that corresponds to each peak maximum along a line that parallels the x-axis of each separation. Alternatively, with a chromatographic data system, the peak maxima can be assigned migration times relative to the origin of the separation and the average peak spacing can be determined by subtraction of the migration times of adjacent peaks. It should be noted that the average peak spacing changes over the course of the separation, with larger average peak spacing early in the separation and progressively smaller peak spacing occurring later in the separation. It should also be noted that peak spacing for some selected pairs of peaks in a given separation may differ significantly from the average peak spacing for the majority of neighboring peaks in the separation.

Once the realtive peak spacing is determined over the course of the separations, the separation data are converted into a set of patterns which are termed "sequence strings". These sequence strings are generated by using the peak spacings to define a string of cells, each cell corresponding to a predicted peak position in the separations. For example, if a peak occurs in a separation in the time slot corresponding to a cell, then the cell is assigned a value of zero, "0". However, if there is no peak in the time slot corresponding to a given cell, the cell is assigned a value of one, "1". This logic was chosen since the absence of a peak in a given separation is indicative of the presence of the nucleotide corresponding to the particular 2',3'-dideoxynucleoside 5'-triphosphate omitted from the three component ddNTP terminator reaction mixture corresponding to that separation. Thus, "1" corresponds to the particular base coded for in that particular sequencing mixture and "0" corresponds to one of the other three bases, the exact identity of which is unknown at this stage. Using this procedure, four sequence strings are generated, one for each of the four sequencing mixtures. These sequence strings are then combined to form a 4 row by X column array, where X is the maximum number of cells in the longest of the sequence strings.

At this point, four sequence strings have been generated but are not aligned. Any of a number of simple alignment algorithms can be used to effect the alignment and allow deduction of the final sequence. For example, a "shotgun" alignment procedure could be used in which all possible combinations of alignments of the columns in the four sequence strings are tested for conflicts. Conflicts include the absence of a peak or the presence of more than one peak in a column of the sequence string array. Computer alignment algorithms based on those used in alignment/assembly software programs for DNA sequencing might be developed to facilitate alignment of the sequence strings as well.

For the purpose of illustration, a manual alignment algorithm as described below can be implemented. Alignment can be started by attempting to align the A and C rows in a 2-row array of the sequence strings. The data in the C row of the 2-row array is shifted one column to the right and the entries in each column of the 2-row array summed together in a summation row. If the entries of every cell of the summation row equal one or zero, then this particular configuration is deemed an "aligned configuration" and stored for further testing with the remaining two rows of data (the G row and the T row). The data in the second row of the 2-row array is sequentially shifted one cell to the right for a maximum of 10 shifts and retested for alignment after each shifting, saving aligned configurations. A maximum of 10 shifts is usually sufficient since the four separations used to generate the data are usually roughly aligned. The data for the first two rows (the A row and the C row) are then returned to the original starting configuration and tested for additional aligned configurations by sequentially shifting the data in row C one cell to the left, using the same alignment criteria and saving only the "aligned" configurations.

The saved "aligned" configurations that are generated from the A and C rows above are then tested for alignment in a 3-row array with the G row by shifting the data in the G row sequentially by one cell and testing for alignment with the "aligned" configurations of the A and C rows. "Aligned" configurations generated by this process are again saved. This process is then repeated with the T row and the final "aligned" configurations are saved as the sequence.

It should be noted that as the length of the sequence string data becomes longer, the probability of more than one unique alignment for any two rows (e.g. the A and C row) becomes smaller. Thus, if the sequence strings contain ~100 cells, only one "aligned" configuration might be obtained for any two sequence strings.

The method of the invention is also useful as a general alignment procedure of nucleic acid sequencing fragments produced by a number of methods and run together in a single separation or run in multiple separations. For example, the method is applicable to alignment of separations of nucleic acid sequencing fragments run in parallel in individual electrophoretic media but which are misaligned due to offset distortions.

In addition, the method could be applied to alignment of separations of nucleic acid fragments that are misaligned due to mobility differences among the various sets of fragments arising from the use of different detection labels used for coding the various nucleotides in the sequencing reaction. Currently, four different fluorophore labels are used to code for A, C, G and T bases in Sanger-type sequencing reactions. Because of the color-coding feature, the four sets of sequencing reaction fragments can be mixed together and run simultaneously in a single lane of an electrophoretic gel or a single capillary by capillary electrophoresis. Separation in a single electrophoretic run minimizes many of the offset distortions described earlier. Careful selection of the four fluorophore labels used to color code the fragments is important since the four fluorophores must be sufficiently different in spectral characteristics to permit differentiation among the labels but the labels must be chemically similar so as not to impart significant mobility differences to the various sets of fragments. Since the spectral characterisitics of the labels are related to their chemical composition, a delicate compromise between maximum visual discrimination and minimal electrophoretic mobility differences must be reached for the four labels. Typically, closely-related analogs of a parent fluorophore possessing fluorescent emission maxima that are only 20–50 nm apart are selected for sequencing applications. Thus, spectral discrimination among the labeled fragments and correct assignment of base identity to each electrophoretic band is difficult.

The method of the present invention, however, could be applied to alignment of electrophoretic separations of sets of sequencing fragments that are coded with detection labels of widely differing chemical composition and thus different spectral characteristics. Four sets of sequencing fragments (set A=fragments terminated by the ddC, ddG, ddT mix; set C=fragments terminated by the ddA, ddG, ddT mix; set G=fragments terminated by the ddA, ddC, ddT mix; set T=fragments terminated by the ddA, ddC, ddG mix) could be produced such that each fragment in a set would be color-coded so that fragments terminated by the same ddNTP in any set would contain the same detection label, but each fragment type within a set would be distinguishable by a different detection label. These four sets of fragments could then be mixed together and analyzed in a single electrophoretic separation, using the color-coded feature of the labels to distinguish between the different ddNTP terminated fragments. Because the requirement of negligible mobility shift differences among the labels has been diminished, the four labels can vary significantly in chemical nature and thus can vary in spectral characteristics. For example, a fluorescein-type label could be used for the A nucleotide in the ddC, ddG, ddT fragment sets, a rhodamine-type label could be used for the C nucleotide in the ddA, ddG, ddT fragment sets, a cyanine-type label could be used for the G nucleotide in the ddA, ddC, ddT fragment sets and a nitrobenzoxadiazole-type label could be used for the T nucleotide in the ddA, ddC, ddG fragment sets. Using this approach, throughput of the separation step is increased by a factor of four, since the four sets of fragments can now be analyzed simultaneously in a single electrophoretic separation.

In another implementation, the method described in the instant invention can be used to increase throughput in nucleic acid sequencing by allowing multiple template nucleic acids to be processed simultaneously. In the proposed protocol, four or more sets of sequencing reactions, each containing three of the four 2',3'-dideoxynucleoside 5'-triphosphate terminators would be prepared for each DNA template in the same way as described above. However, a unique detection label would be associated with each template nucleic acid, such that all fragments from template #1 might be associated with a fluorescein label and all fragments from template #2 might be associated with a rhodamine label. Upon completion of the sequencing reactions the set A fragments, terminated by the ddC, ddG, ddT mix, from each template are mixed together and electrophoresed in a common electrophoretic separation. Likewise, the set C fragments, from all templates would be mixed together and electrophoresed in a common electrophoretic separation. Likewise, the set G fragments, terminated by the ddA, ddC, ddT mix, from all templates would be mixed together and electrophoresed and the set T fragment from all templates mixed and electrophoresed. The multi-template mixtures could be electrophoresed in parallel electrophoretic runs or electrophoresed in serial runs on the same electrophoretic medium. Because of the color-coding feature of this approach, the electrophoretic band patterns for each set of sequencing fragments for each template can be identified based on the spectral characteristics of the bands in the separations. Thus, the set A, set C, set G and set T fragments for template #1 which may have been labeled with a fluorescein-type label can be distinguished from template #2. Data for both sequences can be simultaneously extracted from the electrophoretic separations and subsequently aligned using the method of the invention.

EXAMPLES

Example 1

Four multi-component sequencing fragment mixtures were prepared by annealing 12.5 $\mu$L of 200 ng/mL single-stranded M13mp18 template DNA (United States Biochemical Corporation, Cleveland Ohio) with 2.5 µL of 1 picomole/ µL fluorescein-tagged primer Fluoro-FAM -21 primer, Keystone Scientific, Menlo Park, Calif.) in the presence of 1× Sequencing Buffer (40 mM Tris-HCl, pH 7.5, 20 mM $MgCl_2$, 50 mM NaCl, United States Biochemical Corporation, Cleveland Ohio) in a total volume of 25 µL. The mixture was heated to 65–68° C. for two minutes in a water bath, after which the mixture was allowed to cool to room temperature (25° C.) in the water bath over the course of two hours under subdued light conditions.

Reagents for four sets of termination reactions were prepared as follows. To four separate 600 µL. Eppendorf™ microtubes were added 1.25 µL of each of the three 2',3'-dideoxynucleoside 5'-triphosphate terminator solutions (United States Biochemical Corporation, Cleveland Ohio) such that four unique terminator mixtures were produced. Each vial was 80 µM in each of the four dNTPs and 2.66 µM in each of the three appropriate ddNTPs. Set A contained the ddC, ddG, ddT mixture, set. C contained the ddA, ddG, ddT mixture, set G contained ddA, ddC, ddT and set T contained ddA, ddC and ddG.

An enzyme stock solution was prepared in a 600 µL Eppendorf™ microtube by mixing 1.5 µL of 13 units/µL Sequenase™ Ver. 2.0 DNA polymerase (United States Biochemical Corporatiorn Cleveland Ohio), 1.5 µL of 5 units/µL pyrophosphatase (United States Biochemical Corporation, Cleveland Ohio) and 9 µL of glycerol enzyme dilution buffer (20 mM Tris-HCl, pH 7.5, 2 mM DTT (dithiothreitol), 0.1 mM EDTA (ethylenediamnine-tetraacetic acid), 50% glycerol, United States Biochemical Corporation, Cleveland Ohio) in an ice bath. A 5 µL aliquot of this enzyme stock solution and 2.5 µL of 100 mM DTT solution (United States Biochemical Corporation, Cleveland Ohio) were then added to the cooled annealed DNA solution, and the mixture was stored on ice until use.

The set of four terminator reaction mixtures was then briefly warmed to 37° C. in a water bath, after which 5 µL aliquots of the annealed DNA/enzyme preparation were added to each of the terminator reaction mixtures (sets A, C, G, T). The reaction mixtures were then mixed, centrifuged briefly to collect the fluid at the bottom of the reaction tubes, and incubated for 5 minutes at 37° C. in the water bath. At the end of the incubation, 6 µL of stop solution (95% formamide, 20 mM EDTA) was added to each reaction tube, the contents mixed, and collected at the bottom of the tube by brief centrifugation. The sequencing mixtures were then heated for 2 minutes at 80° C. in a hot water bath, after which the denatured mixtures were quick-chilled and stored in an ice-slurry bath.

Separation of the four sequencing mixtures as shown in FIG. 1 was accomplished by serial analysis in a single capillary electrophoresis column. The capillary column was a 10 cm long section of polyimide-clad fused silica (Polymicro Technologies, Phoenix, Ariz.), with a detection window cut in the polyimide cladding 7.0 cm from the injection (cathode) end. The internal bore of the capillary was 100 µm, and had been coated with a layer of polyacrylamide to suppress the electroosmotic flow. The capillary was filled with a polymer-based sieving matrix which consisted of 5.5% linear polyacrylamide in a supporting electrolyte of 1× TBE (89.5 mM tris-[hydroxymethyl] aminomethane, Trizma™, Sigma Chemical Co., St. Louis Mo., 89.5 mM boric acid (Malinckrodt Specialty Chemicals, Paris Ky.), and 2.0 mM EDTA, $Na^+_2$(Sigma Chemnical Co., St. Louis Mo.) and 7 M urea (UltraPure grade, United States Biochemical Corporation, Cleveland Ohio). The linear polyacrylamide was prepared by dissolving 5.5% (w/v) acrylamide (Sigma Chemical Co., St. Louis Mo.) in a 1× TBE/7M urea solution, degassing the resulting solution under 23–25 in. Hg vacuum for 1 hour with sonication, and then initiating the polymerization reaction via addition of aliquots of 10% (w/v) ammonium persulfate and TEMED (N-,N-,N'-,N'-tetramethylethylenediamine).

The resulting fluid polymer-based sieving matrix was loaded into the capillary via a 0.5 mL disposable syringe connected to one end of the capillary by a short section of Teflon™ tubing. The anode end of the loaded capillary was immersed in an aliquot of the sieving polymer solution, whereas the cathode or injection end of the capillary was immersed in a solution of 1× TBE containing 7 M urea.

The process of injecting a sequencing sample mixture into the capillary consisted of removing the 1× TBE/7M urea solution from the cathode end of the capillary, rinsing the capillary end with water, and then immersing the end of the capillary in a 3 µL aliquot of the denatured, chilled sequencing mixture prepared above. The sample was electroinjected at 3 kV (monitored at ~35 µA) for a duration of 30 seconds. Excess sample was rinsed from the end of the capillary with 200 µL of 1× TBE/7M urea buffer. Separation was accomplished by applying a 2 kV potential (200 V/cm), from a Bertan Instruments Model 230 (Hicksville, N.Y.) power supply across the capillary with the injection end immersed in the 1× TBE/7M urea solution. The current through the capillary was monitored at ~23 µA.

The separated fragments were detected by monitoring the fluorescence emanating from the capillary detection window with a Nikon Optiphot confocal microscope. The excitation wavelength was 488 nm and the emission was defined by a 520 nm long-pass filter. A 100 µm×30 µm section of the detector window was imaged via an adjustable spatial filter onto a Hamamatsu Model 928P photomultiplier (Hamamatsu Corporation, Hamamatsu City, Japan) for monitoring the separation. The signal from the PMT was digitized and stored on a Model 1020 PE/Nelson data system (Applied Biosystems, Inc. Foster City Calif.). Data collection was at 5 Hz.

The four separations corresponding to the four 3-component sequencing mixes are only roughly aligned in FIG. 1. FIG. 1A shows the separation of the set A sequencing mixture which contained eqimolar concentrations of the ddC, ddG, and ddT terminators. This separation can be used to deduce the sequencing information for the dA nucleotide component of the template DNA. Likewise, FIG. 1B shows the separation of the set C mixture (ddA, ddG, ddT terminators) and can be used to deduce the sequence information for the dC nucleotide component of the template DNA. FIG. 1C shows the separation of the set G sequencing mixture which contained eqimolar concentrations of the ddA, ddC, and ddT terminators. This separation can be used to deduce the sequencing information for the dG nucleotide component of the template DNA. FIG. 1D shows the separation of the set T mixture (ddA, ddC, ddG terminators) and can be used to deduce the sequence information for the dT nucleotide component of the template DNA.

Tick marks corresponding to the maxima of the individual peaks in each of the four separations are shown just above the abscissa of each separation to define peak spacing. Gaps in the peak spacing pattern are indicative of the absence of a peak corresponding to the 2',3'-dideoxynucleoside 5'-triphosphate omitted from that particular sequencing mixture. Since the peak spacing is approximately constant in a given region of the separation, the magnitude of the gap is indicative of the number of missing peaks in any particular gap. Thus, if the gap width is approximately twice as large as the average peak spacing in a particular region of the separation, then a single peak is missing from the separation and a negative tick mark can be assigned to the gap. If the width of the gap is three times the average peak spacing as judged from nearby peaks, then two peaks are missing from the separation and two negative tick marks can be assigned to the gap. Using this algorithm, a sequencing pattern can be deduced from the peak spacings and the gaps, with a numeric zero assigned to each positive tick that corresponds to a peak in the separation and a numeric one assigned to each negative tick that corresponds to the absence of a peak in the separation. In this way a sequence string pattern can be derived from each of the separations shown in FIG. 1. These sequence string patterns are shown above the abscissa in each of the separations in FIG. 1.

Figure 2A:
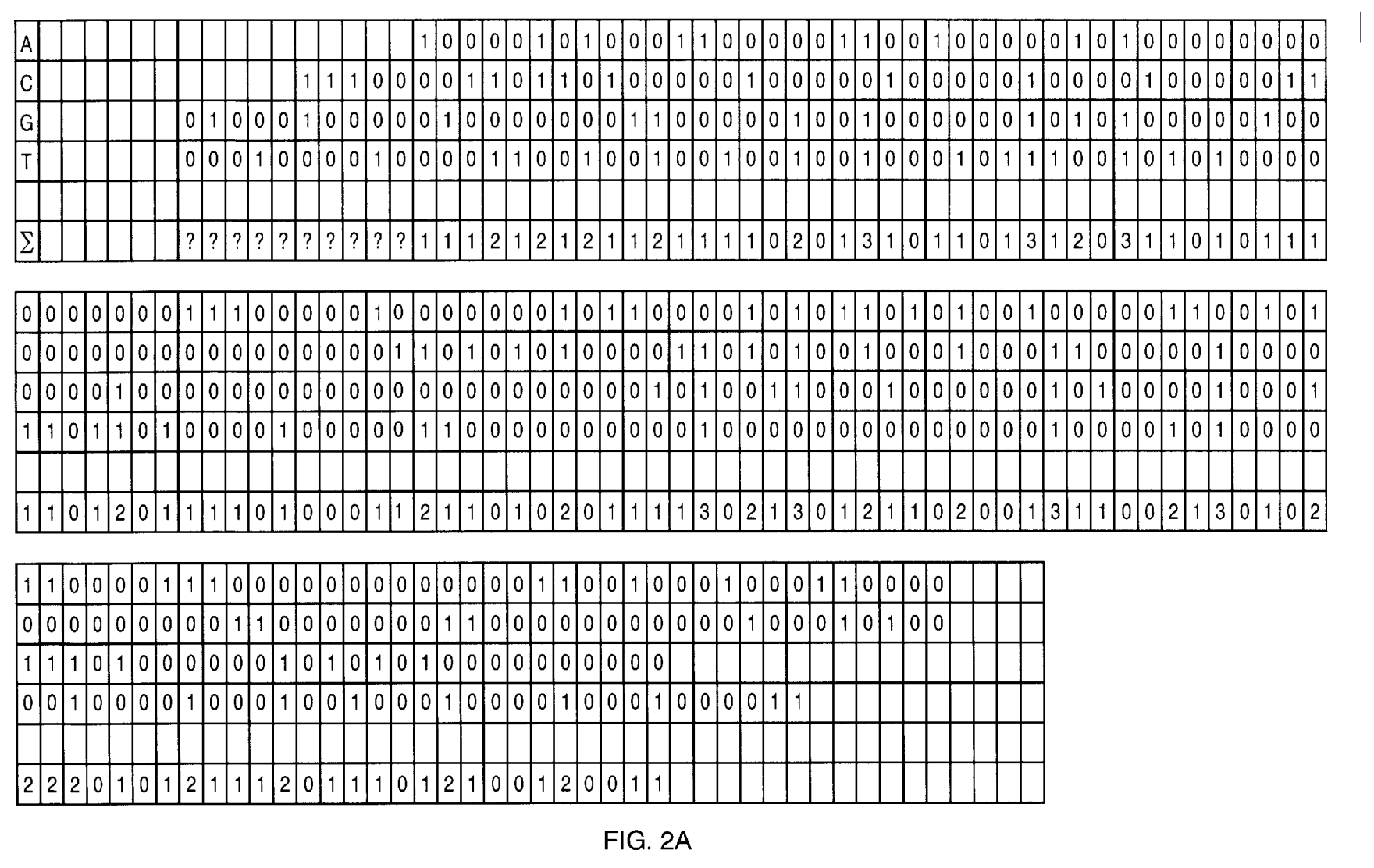
Figure 2B:
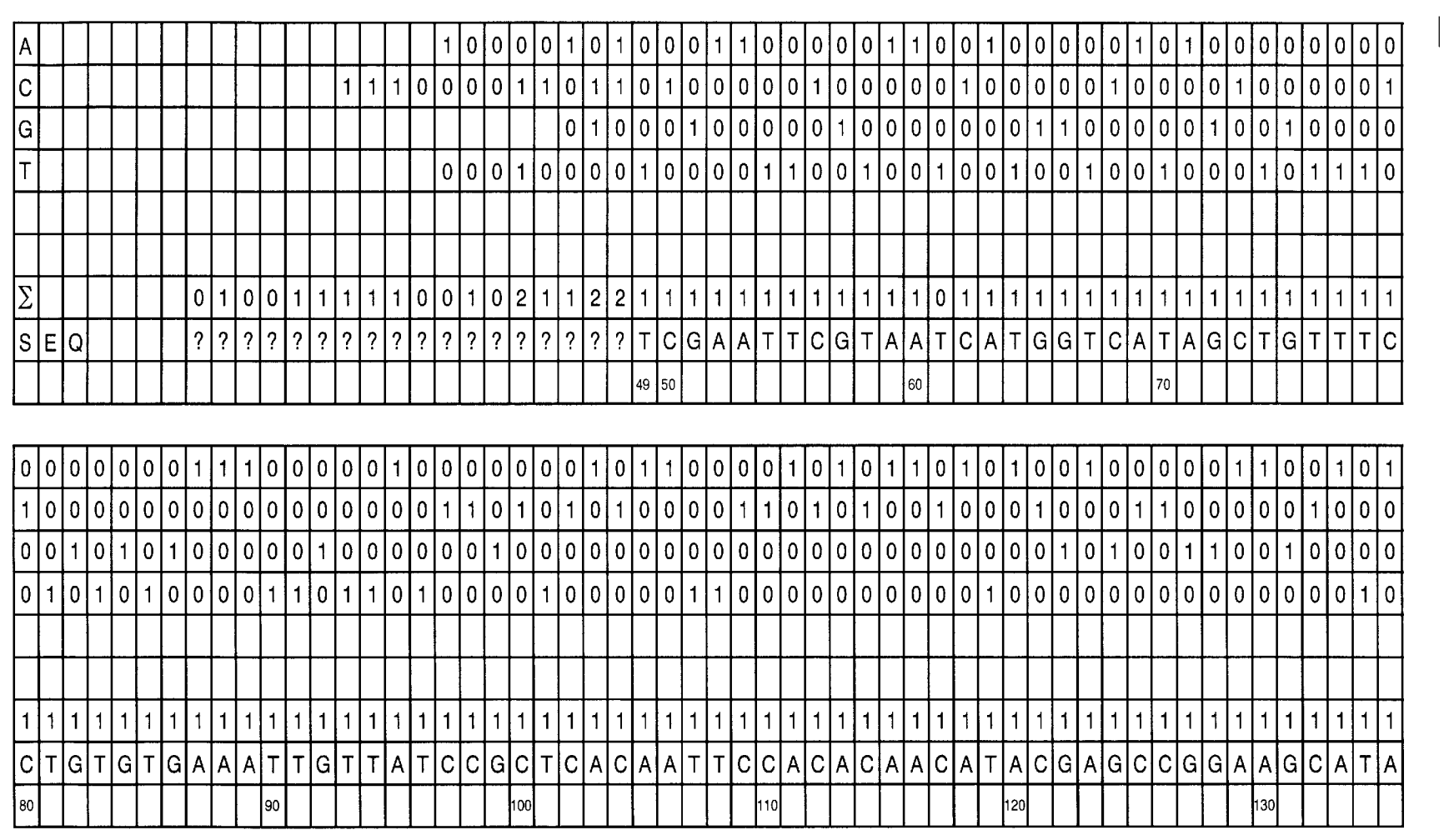
Figure 2C:
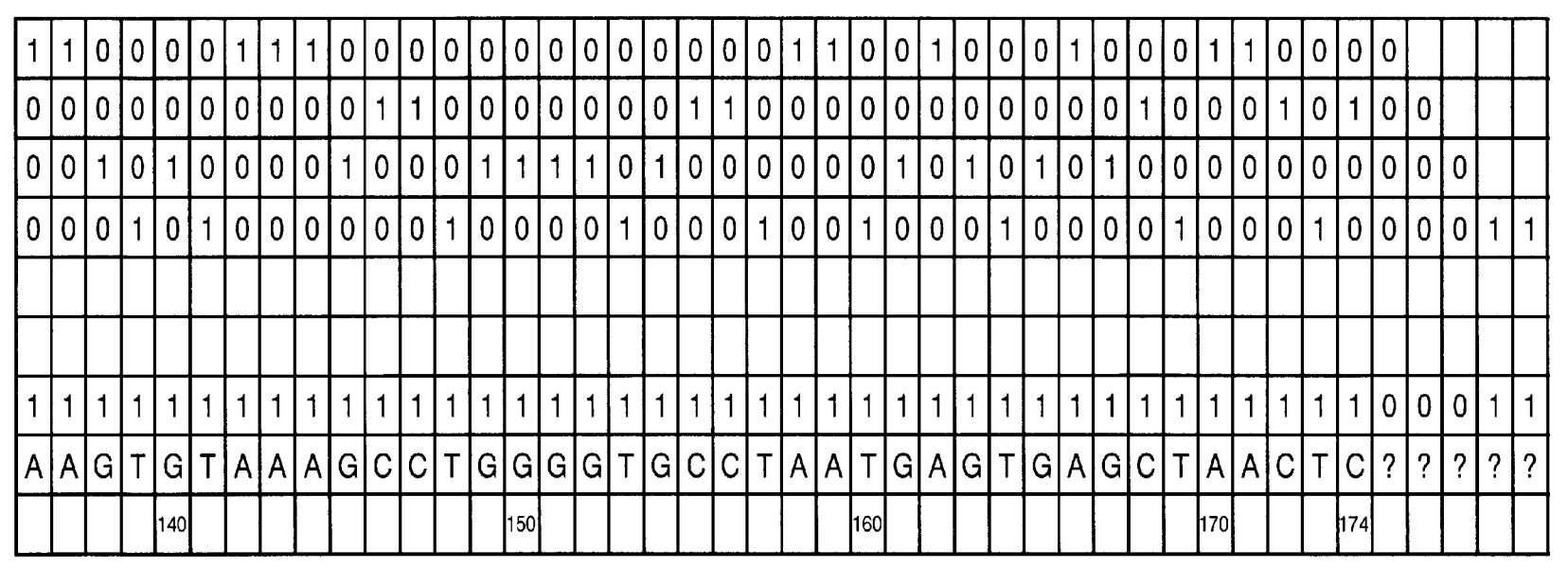

FIG. 2 illustrates the sequence string patterns derived from the separations shown in FIG. 1. FIG. 2A shows the four sequence string patterns derived from the four separations in FIG. 1 Each row represents one of the bases (A, C, G, or T), with a numeric one assigned to each missing peak in each of the separations of FIG. 1. Each sequence pattern is identified by the proper deoxynucleotide letter (ACGT) in column 1 of the array of FIG. 2. FIG. 2A illustrates the sequence string patterns as read from the abscissa of the separations in FIG. 1 and no alignment has taken place.

FIG. 2B illustrates the proper alignment of the four sequence patterns from FIG. 2A. obtained from a simple alignment algorithm. The aligned portion of the sequence strings is highlighted in FIG. 2B. Correct alignment occurs when each column of the pattern is summed together and each column sums to one, indicating that one and only one peak has been assigned to each column. Thus, it is evident from the summation (Σ) row of FIG. 2B that correct alignment has been achieved for a lengthy stretch of sequence in the center of the sequence patterns. The first 10 or so columns do not sum to "one" and sequence information cannot be obtained from these. This is a result of inadequate separation of the peaks in the early portion of the four separations where the peaks migrate just behind the residual labeled primer peak. The last 10 or so columns also do not sum to "one" and sequence information cannot be obtained from these data. This is a result of inadequate resolution of the peaks at the end of the separations in FIG. 1. However, a lengthy stretch in the middle of the sequence patterns can be aligned and thus a sequence can be read from the top four rows of FIG. 2B. The sequence as determined by this procedure is shown in the bottom row of FIG. 2B. The sequence information is accurate over the region of 48 to 174 bases when compared with the known sequence of M13mp18 DNA.

Figure 3A:
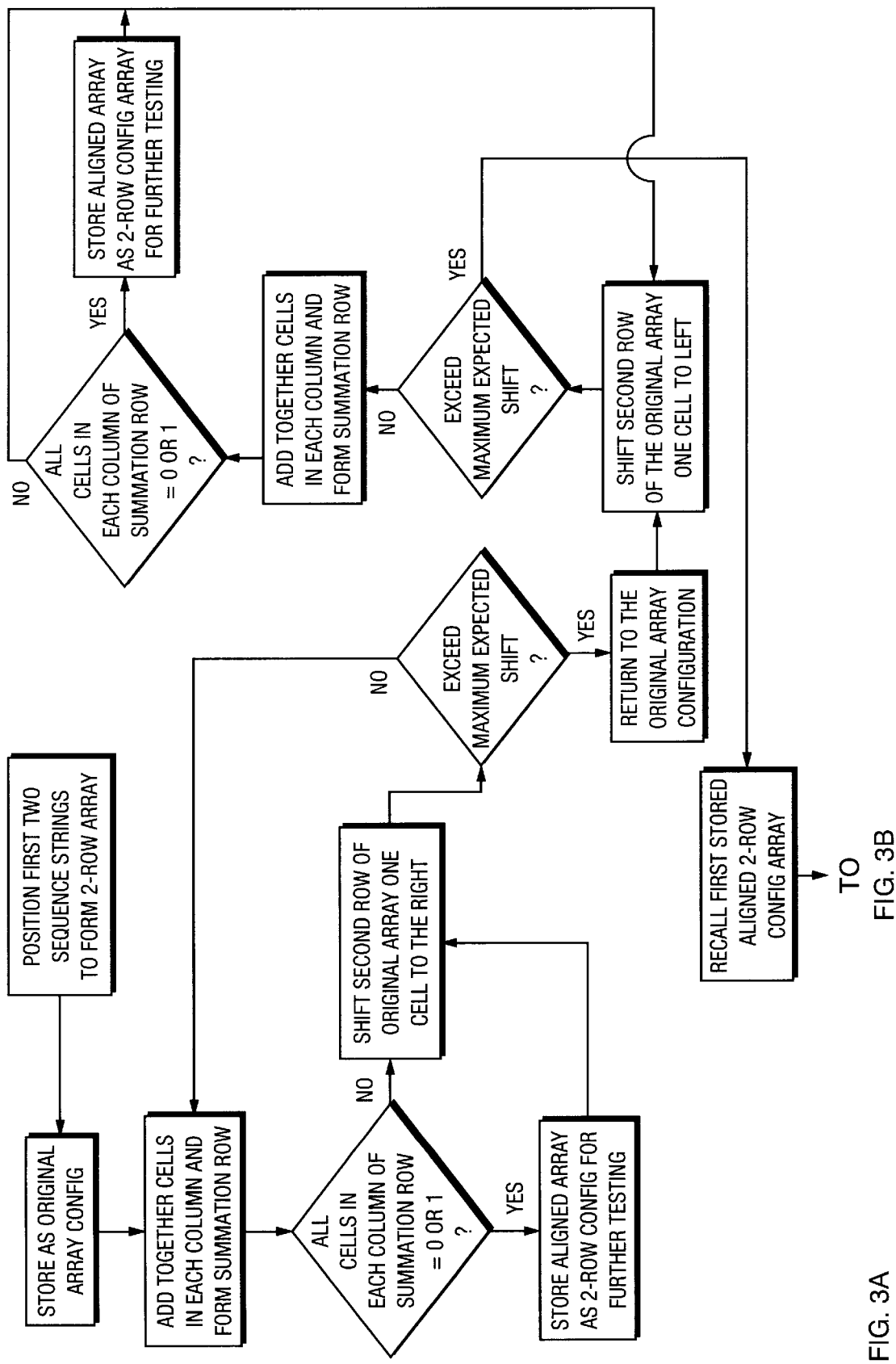
FIGS. 3A–C illustrates a simple algorithm useful for deducing the DNA template sequence information from the separation patterns and sequence strings illustrated in FIGS. 1 and 2 of the instant invention.
Figure 3B:
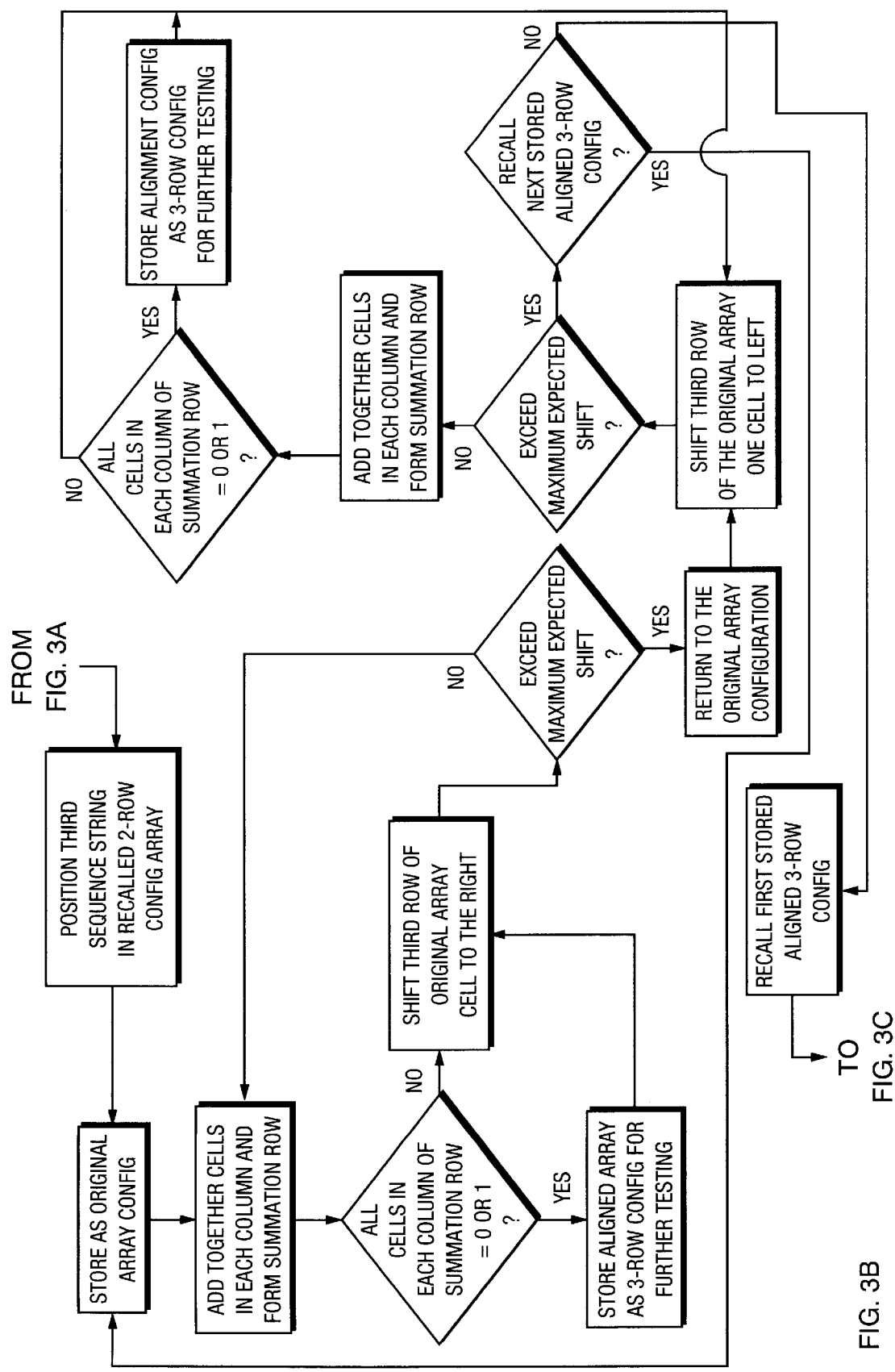
Figure 3C:
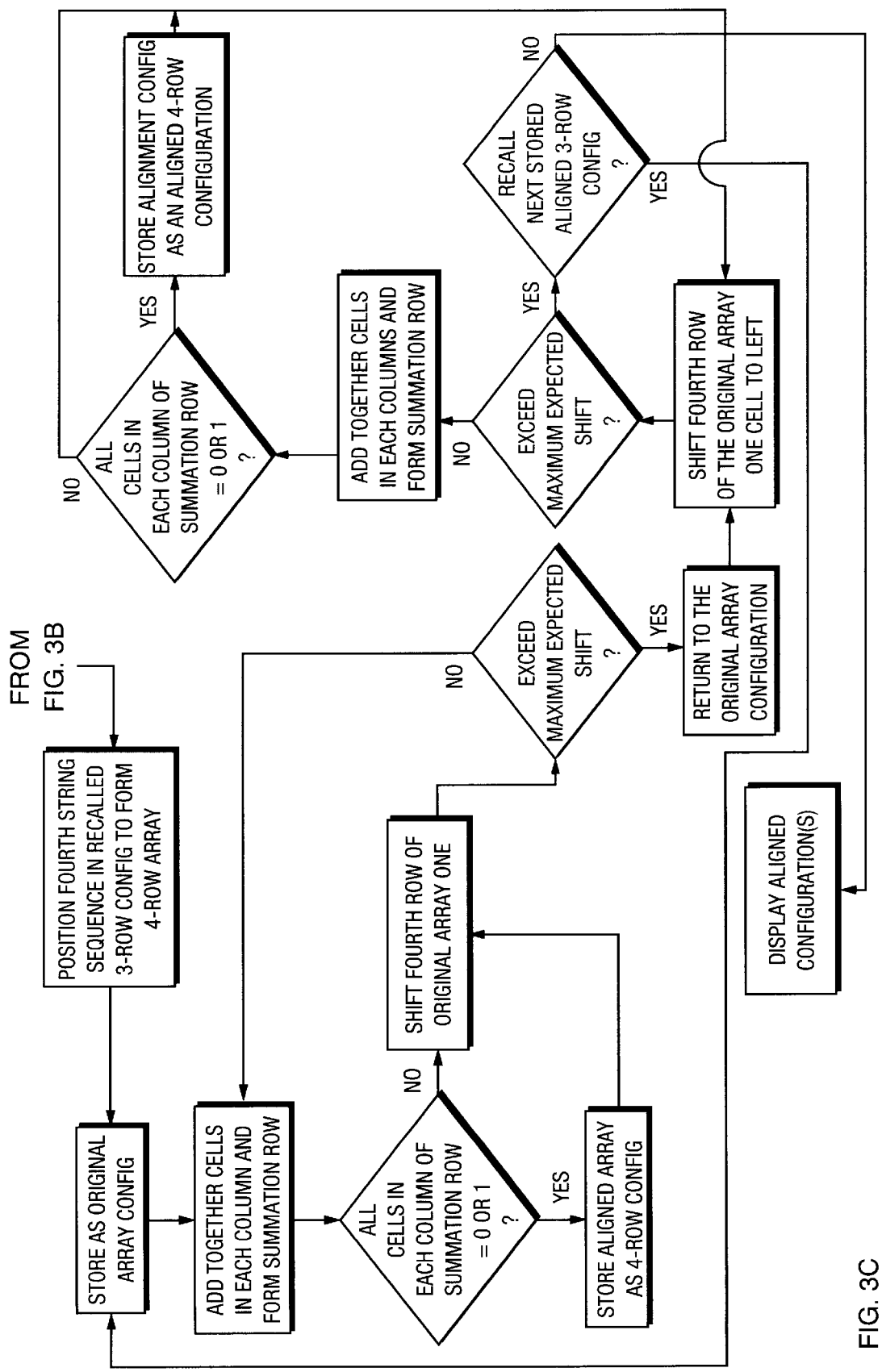

FIG. 3 illustrates the simple alignment algorithm used to effect the alignment shown in FIG. 2B. Initial alignment of the A and C rows of the array is shown in FIG. 2A. The data in Row C of the two row array was shifted one column to the right and the entries in each column summed. The entries of the cells of the summation row equaled one for a long stretch of cells, and thus this particular configuration was deemed an aligned configuration and stored for further testing with the remaining two rows of data. The data in the second row was sequentially shifted one cell to the right for a maximum of 10 shifts and retested for alignment after each shifting, saving aligned configurations. The data was then returned to the original configuration (as illustrated in FIG. 2A) and tested by sequentially shifting the data in row C one cell to the left and testing for alignment, saving aligned configurations. Only one aligned configuration was found from the 21 tested configurations as described above.

The saved aligned configuration from above for rows A and C was then tested in the same manner in a 3-row array by shifting the data in row G by one cell and testing for alignment. Aligned configurations were saved. This process was then repeated with row T and the final aligned configuration is shown in FIG. 2B. The steps in the alignment process are outlined in the algorithm flow chart shown in FIGS. 3A–C and this algorithm was implemented in a Microsoft Excel™ spreadsheet.

Example 2

This example illustrates application of an embodiment of the instant invention for sequencing a single template DNA using a four-color coding scheme for identifying the four bases in the separation. Four individual multi-component sequencing fragment mixtures are prepared by annealing one of four fluorescently-tagged primers to one of four aliquots of the single-stranded template DNA to be sequenced. Each of the tagged primers has a different fluorescent label attached near or on the 5'-end of the primer. The nucleic acid sequence of all the primers is identical since it is desired that the primer "prime" the extension reactions at the same point in each base-associated mixture. A suitable primer nucleic acid sequence for use with M13mp18-derived template DNA is 5'-TGT-AAA-ACG-ACG-GCC-AGT-3'. Fluorescent labels suitable for coupling to or near the 5' end of the primers for detection purposes include 6-carboxy-X-rhodamine (ROX), Texas Red™, fluorescein (FITC), tetramethylrhodamine (TAMRA), CY3™, CY5™, NBD, lissamine rhodamine B, Bo-dipy, etc. Labeled primers suitable for implementing the protocol described in this example are readily available from a number of suppliers, including Bio-Synthesis, Inc. (Lewisville, Tex.), Genemed Biotechnologies, Inc. (South San Francisco, Calif.), Genosys Biotechnologies, Inc. (The Woodlands, Tex.), Genset, Inc. (La Jolla, Calif.), Keystone Laboratories, Inc. (Menlo Park, Calif.), National Biosciences, Inc. (Plymouth, Minn.), and Perkin Elmer/Applied Biosystems, Inc. (Foster City, Calif.). The four fluorescent labels are chosen such that they are readily spectrally-distinguishable from each other. The four tagged primers anneal to individual aliquots of the template nucleic acid under conditions such that a stable primer-template hybrid is formed. Suitable hybridization conditions for forinig such a hybrid utilize a buffer containing 40 mM Tris-HCl, pH 7.5, 20 mM $MgCl_2$, and 50 mM NaCl. The mixtures are heated to 65–68° C. for several minutes in a water bath, after which the mixtures are cooled to room temperature (25° C.) in the water bath over the course of at least ½ hour under subdued light conditions to preserve stability of the fluorescent labels. Concentrations of primer and template nucleic acids used in this protocol can vary, but representative concentrations are 12.5 μL of 200 ng/mL template DNA with 2.5 μL of 1 picomole/mL tagged primer in a total volume of 25 μL.

Next, reagents for a set of 4 termination reactions are prepared as follows. 1.25 μL of each of the three 2',3'-dideoxynucleoside 5'-triphosphate terminator solutions is added to four separate tubes such that 4 unique terminator mixtures are produced. Concentrations of dNTs and ddNTs can vary but a representative concentration is 80 μM of each of the four dNTPs and 2.66 μM of each of the appropriate 3 ddNTPs. The four termination mixtures are composed in a manner analogous to those described in Example 1 above, i.e. sample "ddACG" contains the ddA, ddC, ddG mixture, sample "ddACT" contains the ddA, ddC, ddT mixture, etc.

An enzyme stock solution is prepared in a microtube by mixing several microliters of suitable concentrations of enzymes (e.g., Sequenase™ Ver. 2.0 DNA polymerase and pyrophosphatase, available from United States Biochemical Corporation, Cleveland Ohio) in a suitable buffer (e.g., 50% glycerol, 20 mM Tris-HCl, pH 7.5, 2 mM DTT (dithiothreitol), 0.1 mM EDTA (ethylenediamine-tetraacetic acid) in an ice bath. An aliquot of this enzyme stock solution and an aliquot of 100 mM DTT solution are be added to each of the cooled annealed DNA solutions prepared above, and the mixtures is stored on ice until use.

The set of four terminator reaction mixtures prepared as described above are briefly warmed to 37° C. in a water bath, after which each of the annealed DNA/enzyme preparations described above is added to the corresponding terminator reaction mixture (samples ddACG, ddACT, ddAGT, ddCGT). After brief mixing and centrifugation to collect the combined fluids at the bottom of the reaction tubes, the mixtures are incubated for 5 minutes at 37° C. in the water bath. At the end of the incubation, a few microliters of a stop solution (e.g., 95% formamide, 20 mM EDTA) is added to each reaction tube, and the contents should be mixed and collected at the bottom of the tube by brief centrifugation. The four sequencing mixtures thus prepared are then combined into one microtube and then heated for 2 minutes at 80° C. in a hot water bath, after which the combined denatured mixtures are quick-chilled and stored until use in an ice-slurry bath.

Separation of the combined sequencing mixtures can be accomplished by analysis in a single capillary electrophoresis column. A suitable capillary column, a method for its preparation, and a method for running the separation are described in Example 1 of this specification.

Detection of the separated fragments in the combined mixtures is accomplished by monitoring the fluorescence from the detection window of the capillary using a modification of the instrument setup as described in Example 1. Four optical filters and four photomultiplier tubes is required to monitor the four "colors" from the four fluorescent labels in the sequencing fragments as the various fragments migrate past the detection window on the capillary. A single excitation wavelength can be used to excite all four labels if labels are judiciously chosen such that they possess comparable absorbance spectra; otherwise, excitation wavelengths should be employed such that each fluor is efficiently excited by at least one of the excitation wavelengths. Detection requires the use of four optical filters and these filters are chosen such that each of the filters efficiently passes emitted radiation corresponding to the wavelength of one of the fluorescent labels and efficiently blocks both radiation of the excitation wavelength(s) as well as radiation of wavelengths associated with the other three fluorescent labels.

Separation of the combined mixtures of fragments produced by the described protocol will yield 4 unique separation patterns, each corresponding to one of the four original sequencing fragment mixtures. The identity of the sequencing fragment mixture (e.g. the ddACG, ddACT, ddAGT, or ddCGT mixture) to which each separation pattern corresponds can be ascertained from the "color" of the fragments in each separation pattern, since the fragments in each of the original sequencing fragment mixtures are associated with a unique fluorescently-labeled primer. Means and method for processing the four separation patterns generated from the four-color, multi-component mixtures have been described in Example 1 of this specification. Means and method for generating the four sequence strings and subsequent alignment of the sequence strings can be taken from Example 1 without modification. The embodiment of this example differs from that of Example 1 only in that a single separation is run to analyze the four multi-component sequencing mixtures and each of the four sequencing mixtures is uniquely associated with a single base via the unique fluorescent label on the primer used to generate the mixture.

Example 3

This example illustrates application of an embodiment of the instant invention for sequencing multiple DNA templates using a multi-color coding scheme for identifying the various fragments in the separations associated with each template. To implement this embodiment of the invention, four individual single-color, multi-component sequencing fragment mixtures are prepared for each template DNA by annealing a different fluorescently-tagged primer to each of the single-stranded template DNA to be sequenced. Each of the tagged primers has a different fluorescent label attached near or on the 5'-end of the primer. The nucleic acid sequence of the primers for the various template DNA could be but are not necessarily all identical since it is not necessary that the primer "prime" the extension reactions for all the different template DNA at the same point. Fluorescent labels suitable for coupling to or near the 5' end of the primer for detection purposes include 6-carboxy-X-rhodamine (ROX), Texas Red™, fluorescein (FITC), tetramethylrhodamine (TAMRA), CY3™, CY5™, NBD, Lissamine Rhodamine B, Bo-Dipy, etc., and suitable labeled primers for use in this regard are readily available from a number of suppliers as listed in Example 2. The various fluorescent labels are chosen such that they are readily spectrally-distinguishable from each other and thus the fragments in the separations associated with each of the various template DNA can be readily identified by the associated color.

For each template DNA to be sequenced, a stock primer/template mixture would be prepared by annealing an appropriate concentration of one of the primers to an appropriate concentration of that template DNA. The tagged primer should be annealed to the template nucleic acid under conditions such that a stable primer-template hybrid is formed. Suitable hybridization conditions for forming a hybrid might utilize a buffer containing 40 mM Tris-HCl, pH 7.5, 20 mM $MgCl_2$, and 50 mM NaCl. The mixtures are heated to 65–68° C. for several minutes in a water bath, after which the mixture is allowed to cool to room temperature (25° C.) in the water bath over the course of at least ½ hour under subdued light conditions to preserve stability of the fluorescent labels. Concentrations of primer and template nucleic acids can vary, but representative concentrations are 12.5 mL of 200 ng/µL template DNA with 2.5 µL of 1 picomole/µL tagged primer in a total volume of 25 µL. In the strategy used in this embodiment of the invention, a single fluorescent label would be associated with each template DNA as in Example 1, but different labels would be used to distinguish between the various template DNA. For example, template #1 might be identified with a fluorescein label, template #2 might be identified with a rhodamine label, template #3 might be identified with a cyanine label, etc.

For each template DNA to be sequenced, reagents for a set of 4 termination reactions are prepared as follows. 1.25 µL of each of the three 2',3'-dideoxynucleoside 5'-triphosphate terminator solutions is added to each of four mnicrotubes such that four unique terminator mixtures are produced. Concentrations of dNTs and ddNTPs can vary, but a representative concentration is 80 µM of each of the four dNTPs and 2.66 µM for each of the appropriate 3 ddNTP's. The four mixtures are composed in a manner analogous to those described in Example 1 above, i.e. sample "ddACG" for each template DNA would contain the ddA, ddC, ddG mixture, sample "ddACT" would contain the ddA, ddC, ddT mixture, etc.

For each template DNA to be sequenced, an enzyme solution is prepared in a microtube by mixing several microliters of suitable concentrations of enzymes (e.g., Sequenase™ Ver. 2.0 DNA polymerase and pyrophosphatase, available from United States Biochemical Corporation, Cleveland Ohio) in a suitable buffer (e.g., 50% glycerol, 20 mM Tris-HCl, pH 7.5, 2 mM DTT (dithiothreitol), 0.1 mM EDTA (ethylenediamine-tetraacetic acid) in an ice bath. An aliquot of this enzyme stock solution and an aliquot of 100 mM DTT solution is then added to each of the cooled annealed DNA solutions from each of the template DNA as prepared above, and the mixtures are stored on ice until use.

For each of the template DNA to be sequenced, the set of four terminator reaction mixtures prepared as described above is briefly warmed to 37° C. in a water bath, after which an aliquot of the annealed DNA/enzyme preparation described above is added to each of the corresponding terminator reaction mixtures (samples ddACG, ddACT, ddAGT, ddCGT). After brief mixing and centrifugation to collect the combined fluids at the bottom of the reaction tubes, the four mixtures for each template DNA are incubated for 5 minutes at 37° C. in the water bath. At the end of the incubation, a few microliters of a stop solution (e.g., 95% formamide, 20 mM EDTA) is added to each reaction tube, and the contents should be mixed and collected at the bottom of the tube by brief centrifugation.

A set of 4 combined mixtures of sequencing fragment mixtures is prepared. Set #1 is prepared by combining the fragments from the ddACG mixtures derived from each template DNA, set #2 is prepared by combining the fragments from the ddACT mixtures derived from each template DNA, etc. In this way, a set of four mixtures is prepared, and each mixture contains sequencing fragments that will allow the determination of one of the four bases in the template DNA. The set of four combined sequencing fragment mixtures is heated for 2 minutes at 80° C. in a hot water bath, after which the denatured mixtures is quick-chilled and stored until use in an ice-slurry bath.

Separation of the four sequencing mixtures is accomplished by serial analysis in a single capillary electrophoresis column. A suitable capillary column, a method for its preparation, and a method for running the separations are described in Example 1.

Detection of the separated fragments in the combined mixtures is accomplished by monitoring the fluorescence from the detection window of the capillary using a modification of the instrument setup in Example 2. The experimental apparatus will differ only slightly from that described in Example 2 in that an optical filter and a photomultiplier tube will be required to monitor for the label ("color") associated with each of the template DNA to be sequenced. Thus, if six template DNA are being sequenced, then six optical filters and six photomultiplier tubes will be required to monitor the various sets of fragments in the separation step. A single excitation wavelength can be used to excite all of the labels if said labels are judiciously chosen such that they possess comparable absorbance spectra; otherwise, excitation wavelengths should be employed such that each fluor label is efficiently excited by at least one of the excitation wavelengths. Detection requires the use of multiple optical filters and these filters are chosen such that each of the filters efficiently passes emitted radiation corresponding to one of the fluorescent labels and efficiently blocks both radiation of the excitation wavelength(s) as well as radiation of wavelengths associated with the other fluorescent labels.

The set of four separation patterns associated with each template DNA are determined from the "color" of the separation patterns generated above. Means and method for processing the multiple separation patterns generated for each template DNA from the multi-color, multi-component mixtures have been described in Examples 1 and 2. Means and method for generating the four sequence strings and subsequent alignment of the sequence strings can be taken from Examples 1 and 2 without modification.

The foregoing descriptions of the various embodiments of the invention have been presented for purposes of illustration and description. They are not intended to be exhaustive or to limit the invention to the precise form disclosed, and many obvious modifications and variations by those skilled in the art are possible in light of the above teaching.

What is claimed is:

1. A method for obtaining the primary sequence of a nucleic acid template comprising:
   a) preparing, complementary to said nucleic acid template, a set of mixtures of oligonucleotide fragments containing a label, each fragment of a mixture terminated with any single nucleotide terminator selected from a unique two-nucleotide or a unique three-nucleotide terminator combination;
   b) separating the labeled fragments in each mixture of said set of mixtures of oligonucleotide fragments according to length by an electrophoretic means;
   c) detecting the oligonucleotide fragments according to their label in each separated mixture of said set of mixtures;
   d) identifying the relative spacing of said oligonucleotide fragments in each separated mixture of the set of mixtures independent of the separated oligonucleotide fragments in the other mixtures in the set of mixtures;
   e) producing a set of sequence patterns, each sequence pattern in the set of sequence patterns being based on the relative spacing of said oligonucleotide fragments in each single separated mixture independent of the other mixtures in the set of mixtures;
   f) applying an alignment algorithm to said set of sequence patterns.

2. The method of claim 1, where the nucleotide terminators are 2',3'-dideoxynucleoside 5'-triphosphate or analogs thereof.

3. The method of claim 1, where the nucleotide terminators are 3'-deoxynucleoside 5'-triphosphates or analogs thereof.

4. The method of claim 1, where said set of mixtures comprises four mixtures consisting of:
   a) a mixture of labeled oligonucleotide fragments, each fragment of the mixture terminating with any single nucleotide terminator selected from the group consisting of ddA, ddC and one of either ddG or ddI 2',3'-dideoxynucleoside 5'-triphosphate terminators;
   b) a mixture of labeled oligonucleotide fragments, each fragment of the mixture terminating with any single nucleotide terminator selected from the group consisting of ddA, ddC and ddT 2',3'-dideoxynucleoside 5'-triphosphate terminators;
   c) a mixture of labeled oligonucleotide fragments, each fragment of the mixture terminating with any single nucleotide terminator selected from the group consisting of ddA, ddT and one of either ddG or ddI 2',3'-dideoxynucleoside 5'-triphosphate terminators;

d) a mixture of labeled oligonucleotide fragments, each fragment of the mixture terminating with any single nucleotide terminator selected from the group consisting of ddC, ddT and one of either ddG or ddI 2',3'-dideoxynucleoside 5'-triphosphate terminators.

5. The method of claim 1, where said set of mixtures comprises six mixtures consisting of:

a) a mixture of labeled oligonucleotide fragments, each fragment of the mixture terminating with any single nucleotide terminator selected from the group consisting of ddA and ddC 2',3'-dideoxynucleoside 5'-triphosphate terminators;

b) a mixture of labeled oligonucleotide fragments, each fragment of the mixture terminating with any single nucleotide terminator selected from the group consisting of ddA and one of either ddG or ddI 2',3'-dideoxynucleoside 5'-triphosphate terminators;

c) a mixture of labeled oligonucleotide fragments, each fragment of the mixture terminating with any single nucleotide terminator selected from the group consisting of ddA and ddT 2',3'-dideoxynucleoside 5'-triphosphate terminators;

d) a mixture of labeled oligonucleotide fragments, each fragment of the mixture terminating with any single nucleotide terminator selected from the group consisting of ddC and one of either ddG or ddI 2',3'-dideoxynucleoside 5'-triphosphate terminators;

e) a mixture of labeled oligonucleotide fragments, each fragment of the mixture terminating with any single nucleotide terminator selected from the group consisting of ddC and ddT 2',3'-dideoxynucleoside 5'-triphosphate terminators;

f) a mixture of labeled oligonucleotide fragments, each fragment of the mixture terminating with any single nucleotide terminator selected from the group consisting of ddT and one of either ddG or ddI 2',3'-dideoxynucleoside 5'-triphosphate terminators.

6. The method of claim 1, where said set of mixtures comprises four mixtures selected from the group of six mixtures consisting of:

a) a mixture of labeled oligonucleotide fragments, each fragment of the mixture terminating with any single nucleotide terminator selected from the group consisting of ddA and ddC 2',3'-dideoxynucleoside 5'-triphosphate terminators;

b) a mixture of labeled oligonucleotide fragments, each fragment of the mixture terminating with any single nucleotide terminator selected from the group consisting of ddA and one of either ddG or ddI 2',3'-dideoxynucleoside 5'-triphosphate terminators;

c) a mixture of labeled oligonucleotide fragments, each fragment of the mixture terminating with any single nucleotide terminator selected from the group consisting of ddA and ddT 2',3'-dideoxynucleoside 5'-triphosphate terminators;

d) a mixture of labeled oligonucleotide fragments, each fragment of the mixture terminating with any single nucleotide terminator selected from the group consisting of ddC and one of either ddG or ddI 2',3'-dideoxynucleoside 5'-triphosphate terminators;

e) a mixture of labeled oligonucleotide fragments, each fragment of the mixture terminating with any single nucleotide terminator selected from the group consisting of ddC and ddT 2',3'-dideoxynucleoside 5'-triphosphate terminators; and f) a mixture of labeled oligonucleotide fragments, each fragment of the mixture terminating with any single nucleotide terminator selected from the group consisting of ddT and one of either ddG or ddI 2',3'-dideoxynucleoside 5'-triphosphate terminators.

7. The method of claim 1, where said set of mixtures comprises four mixtures consisting of:

a) a mixture of labeled oligonucleotide fragments, each fragment of the mixture terminating with any single nucleotide terminator selected from the group consisting of dA, dC and one of either dG or dI 3'-deoxynucleoside 5'-triphosphate terminators;

b) a mixture of labeled oligonucleotide fragments, each fragment of the mixture terminating with any single nucleotide terminator selected from the group consisting of dA, dC and dT 3'-deoxynucleoside 5'-triphosphate terminators;

c) a mixture of labeled oligonucleotide fragments, each fragment of the mixture terminating with any single nucleotide terminator selected from the group consisting of dA, dT and one of either dG or dI 3'-deoxynucleoside 5'-triphosphate terminators;

d) a mixture of labeled oligonucleotide fragments, each fragment of the mixture terminating with any single nucleotide terminator selected from the group consisting of dC, dT and one of either dG or dI 3'-deoxynucleoside 5'-triphosphate terminators.

8. The method of claim 1, where said set of mixtures comprises six mixtures consisting of:

a) a mixture of labeled oligonucleotide fragments, each fragment of the mixture terminating with any single nucleotide terminator selected from the group consisting of dA and dC 3'-deoxynucleoside 5-triphosphate terminators;

b) a mixture of labeled oligonucleotide fragments, each fragment of the mixture terminating with any single nucleotide terminator selected from the group consisting of dA and one of either dG or dI 3'-deoxynucleoside 5'-triphosphate terminators;

c) a mixture of labeled oligonucleotide fragments, each fragment of the mixture terminating with any single nucleotide terminator selected from the group consisting of dA and dT 3'-deoxynucleoside 5-triphosphate terminators;

d) a mixture of labeled oligonucleotide fragments, each fragment of the mixture terminating with any single nucleotide terminator selected from the group consisting of dC and one of either dG or dI 3'-deoxynucleoside 5'-triphosphate terminators;

e) a mixture of labeled oligonucleotide fragments, each fragment of the mixture terminating with any single nucleotide terminator selected from the group consisting of dC and dT 3'-deoxynucleoside 5'-triphosphate terminators;

f) a mixture of labeled oligonucleotide fragments, each fragment of the mixture terminating with any single nucleotide terminator selected from the group consisting of dT and one of either dG or dI 3'-deoxynucleoside 5'-triphosphate terminators.

9. The method of claim 1, where said set of mixtures comprises four mixtures selected from the group of six mixtures consisting of:

a) a mixture of labeled oligonucleotide fragments, each fragment of the mixture terminating with any single nucleotide terminator selected from the group consisting of dA and dC 3'-deoxynucleoside 5'-triphosphate terminators;

b) a mixture of labeled oligonucleotide fragments, each fragment of the mixture terminating with any single nucleotide terminator selected from the group consisting of dA and one of either dG or dI 3'-deoxynucleoside 5'-triphosphate terminators;

c) a mixture of labeled oligonucleotide fragments, each fragment of the mixture terminating with any single nucleotide terminator selected from the group consisting of dA and dT 3'-deoxynucleoside 5'-triphosphate terminators;

d) a mixture of labeled oligonucleotide fragments, each fragment of the mixture terminating with any single nucleotide terminator selected from the group consisting of dC and one of either dG or dI 3'-deoxynucleoside 5'-triphosphate terminators;

e) a mixture of labeled oligonucleotide fragments, each fragment of the mixture terminating with any single nucleotide terminator selected from the group consisting of dC and dT 3'-deoxynucleoside 5'-triphosphate terminators; and f) a mixture of labeled oligonucleotide fragments, each fragment of the mixture terminating with any single nucleotide terminator selected from the group consisting of dT and one of either dG or dI 3'-deoxynucleoside 5'-triphosphate terminators.

10. The method of claim 1, where the labeled oligonucleotide fragments contain a radioisotope label or a fluorophore label or a chromophore label.

11. The method of claim 1, where the electrophoretic means is slab gel electrophoresis.

12. The method of claim 1, where the electrophoretic means is tube gel electrophoresis.

13. The method of claim 1, where the electrophoretic means is capillary gel electrophoresis.

14. The method of claim 1, where the electrophoretic means is capillary electrophoresis using a sieving polymer matrix.

15. The method of claim 1, where the set of sequence patterns is comprised of a series of two symbols, a first symbol corresponding to the absence of a peak or a signal and a second symbol corresponding to the presence of a peak or a signal.

16. The method of claim 1, where the labeled oligonucleotide fragments in each mixture are present in approximately equal concentrations.

17. A method for obtaining the primary sequence of multiple nucleic acid templates comprising:

a) preparing, complementary to each of said nucleic acid templates, a set of four mixtures of oligonucleotide fragments consisting of set A fragments, set C fragments, set G fragments or set I fragments, and set T fragments, each of the sets of fragments containing a label, each fragment of a mixture terminated with any single nucleotide terminator selected from a unique three-nucleotide terminator combination, and in each mixture from the set of four mixtures derived from a given nucleic acid template, the fragments are associated with a single, unique label which is distinguishable from each of the unique labels associated with the other sets of mixtures of labeled oligonucleotide fragments derived from the other nucleic acid templates;

b) combining the set A fragments from the multiple nucleic acid templates to form a first combined mixture, combining the set C fragments from the multiple nucleic acid templates to form a second combined mixture, combining the set G fragments or the set I fragments from the multiple nucleic acid templates to form a third combined mixture, and combining the set T fragments from the multiple nucleic acid templates to form a fourth combined mixture;

c) separating each of said combined mixtures of oligonucleotide fragments according to length by an electrophoretic means;

d) detecting and distinguishing the oligonucleotide fragments associated with each nucleic acid template in the separations according to the labels;

e) identifying the relative spacing of said oligonucleotide fragments in the separation of each mixture of the set of mixtures associated with each nucleic acid template independent of the other mixtures in the set of mixtures associated with the other nucleic acid templates;

f) producing a set of sequence patterns for each nucleic acid template, each sequence pattern in the set of sequence patterns being based on the relative spacing of said oligonucleotide fragments in the separation of a single mixture of the set of mixtures associated with each nucleic acid template independent of the spacing of the oligonucleotide fragments in the separations of the other mixtures in the set of mixture;

g) applying an alignment algorithm to said set of sequence patterns from each nucleic acid template.

18. The method of claim 17, where the nucleotide terminators are 2',3'-dideoxynucleoside 5'-triphosphates or analogs thereof.

19. The method of claim 17, where the nucleotide terminators are 3'-deoxynucleoside 5'-triphosphates or analogs thereof.

20. The method of claim 17, where said set of mixtures comprises four mixtures consisting of:

a) a mixture of labeled oligonucleotide fragments, each fragment of the mixture terminated with any single nucleotide terminator selected from the group consisting of ddA, ddC and one of either ddG or ddI 2',3'-dideoxynucleoside 5'-triphosphate terminators;

b) a mixture of labeled oligonucleotide fragments, each fragment of the mixture terminated with any single nucleotide terminator selected from the group consisting of ddA, ddC and ddT 2',3'-dideoxynucleoside 5'-triphosphate terminators;

c) a mixture of labeled oligonucleotide fragments, each fragment of the mixture terminated with any single nucleotide terminator selected from the group consisting of ddA, ddT and one of either ddG or ddI 2',3'-dideoxynucleoside 5'-triphosphate terminators;

d) a mixture of labeled oligonucleotide fragments, each fragment of the mixture terminated with any single nucleotide terminator selected from the group consisting of ddC, ddT and one of either ddG or ddI 2',3'-dideoxynucleoside 5'-triphosphate terminators.

21. The method of claim 17, where said set of mixtures comprises four mixtures consisting of:

a) a mixture of labeled oligonucleotide fragments, each fragment of the mixture terminated with any single nucleotide terminator selected from the group consisting of dA, dC and one of either dG or dI 3'-deoxynucleoside 5'-triphosphate terminators;

b) a mixture of labeled oligonucleotide fragments, each fragment of the mixture terminated with any single nucleotide terminator selected from the group consisting of dA, dC and dT 3'-deoxynucleoside 5'-triphosphate terminators;

c) a mixture of labeled oligonucleotide fragments, each fragment of the mixture terminated with any single nucleotide terminator selected from the group consisting of dA, dT and one of either dG or dI 3'-deoxynucleoside 5'-triphosphate terminators;

d) a mixture of labeled oligonucleotide fragments, each fragment of the mixture terminated with any single nucleotide terminator selected from the group consisting of dC, dT and one of either dG or dI 3'-deoxynucleoside 5'-triphosphate terminators.

22. The method of claim 17, where the labeled oligonucleotide fragments contain fluorophore labels or chromophore labels.

23. The method of claim 17, where the electrophoretic means is slab gel electrophoresis.

24. The method of claim 17, where the electrophoretic means is tube gel electrophoresis.

25. The method of claim 17, where the electrophoretic means is capillary gel electrophoresis.

26. The method of claim 17, where the electrophoretic means is capillary electropioresis using a sieving polymer matrix.

27. The method of claim 17, where the sequence pattern is comprised of a series of two symbols, a first symbol corresponding to the absence of a peak or a signal and a second symbol corresponding to the presence of a peak or a signal.

28. The method of claim 17, where the labeled oligonucleotide fragments in each mixture are present in approximately equal concentrations.

* * * * *